US012745897B2

(12) United States Patent
Wang et al.

(10) Patent No.: US 12,745,897 B2
(45) Date of Patent: Sep. 29, 2026

(54) OPTICAL ASSEMBLIES FOR ENDOSCOPIC STEREO VISUALIZATION

(71) Applicant: Cilag GmbH International, Zug (CH)

(72) Inventors: Shaohong Wang, Pleasanton, CA (US); Svitlana Berezhna, Los Gatos, CA (US)

(73) Assignee: Cilag GmbH International, Zug (CH)

( * ) Notice: Subject to any disclaimer, the term of this patent is extended or adjusted under 35 U.S.C. 154(b) by 91 days.

(21) Appl. No.: 18/477,265

(22) Filed: Sep. 28, 2023

(65) Prior Publication Data

US 2025/0107700 A1 Apr. 3, 2025

(51) Int. Cl.

| | |
|---|---|
| ***A61B 1/00*** | (2006.01) |
| ***A61B 1/06*** | (2006.01) |
| ***H04N 13/239*** | (2018.01) |
| ***H04N 23/50*** | (2023.01) |
| ***H04N 23/55*** | (2023.01) |

(52) U.S. Cl.
CPC ...... *A61B 1/00193* (2013.01); *A61B 1/00188* (2013.01); *A61B 1/0646* (2013.01); *H04N 13/239* (2018.05); *H04N 23/55* (2023.01); *H04N 23/555* (2023.01)

(58) Field of Classification Search
CPC ............ A61B 1/00193; A61B 1/00188; A61B 1/0646; H04N 13/239; H04N 23/55; H04N 23/555
See application file for complete search history.

(56) References Cited

U.S. PATENT DOCUMENTS

| | | | | |
|---|---|---|---|---|
| 6,256,155 | B1 * | 7/2001 | Nagaoka | G02B 13/04 359/753 |
| 2014/0336460 | A1 | 11/2014 | Shafer et al. | |
| 2020/0164463 | A1 * | 5/2020 | Shibazaki | B23K 26/064 |
| 2020/0363625 | A1 * | 11/2020 | Baumann | H04N 23/55 |
| 2020/0397223 | A1 * | 12/2020 | Talbert | H04N 23/951 |
| 2020/0404131 | A1 | 12/2020 | Talbert et al. | |
| 2023/0065294 | A1 * | 3/2023 | Intintoli | A61B 1/00163 |
| 2024/0065525 | A1 * | 2/2024 | Regensburger | G02B 21/0012 |

FOREIGN PATENT DOCUMENTS

EP 3329832 A1 6/2018

OTHER PUBLICATIONS

The International Search Report and the Written Opinion of the International Search Authority for International Application No. PCT/IB2024/059321, prepared by the European Patent Office, dated Mar. 7, 2025.

* cited by examiner

*Primary Examiner* — Nasim N Nirjhar
(74) *Attorney, Agent, or Firm* — TechLaw Ventures, PLLC; Terrence J. Edwards

(57) ABSTRACT

Stereo visualization systems with objective lens assemblies for endoscopic visualization. A system include an endoscope tube and an optical assembly disposed within an interior cavity defined by the endoscope tube. The optical assembly includes a negative lens comprising a negative focal length, a positive lens group comprising at least one convex lens, and a beam folding prism that directs a beam of electro-magnetic radiation on to a pixel array of an image sensor.

20 Claims, 27 Drawing Sheets

OPTICAL ASSEMBLIES FOR ENDOSCOPIC STEREO VISUALIZATION

TECHNICAL FIELD

This disclosure is directed to advanced visualization and digital imaging systems and methods and, more particularly but not entirely, to lens assemblies for endoscopic stereo visualization.

BACKGROUND

Stereo visualization, also known as stereoscopic visualization or three-dimensional visualization, offers numerous benefits when applied to surgical procedures, and particularly when utilized by robotic surgical systems. These robotic surgical systems are typically equipped with minimally invasive surgical tools such as endoscopes. Endoscopic surgical instruments are often preferred over traditional open surgical devices because the small incision tends to reduce post-operative recovery time and associated complications. However, the space constrained environment of an endoscope introduces numerous technical challenges when seeking to capture advanced visualization data in a light deficient environment.

It can be desirable to dispose optical components within the endoscope tube itself. These optical components may include lenses, filters, prisms, mirrors, image sensors, and image sensor printed circuit boards. However, the interior space defined by the endoscope tube can be extraordinarily small, in some cases may be smaller than 9 mm. This introduces numerous engineering challenges that are made even more complicated when attempting to dispose dual optical assemblies within the endoscope tube to enable stereoscopic visualization of a scene.

For example, commonly owned U.S. Patent Application Publication No. 2020/0404131, entitled "HYPERSPECTRAL AND FLUORESCENCE IMAGING WITH TOPOLOGY LASER SCANNING IN A LIGHT DEFICIENT ENVIRONMENT," filed on Oct. 24, 2019, which is incorporated by reference in its entirety, describes an endoscopic visualization system for color and "specialty" imaging. In this disclosure, an emitter is configured to emit electromagnetic energy in wavelength bands within the visible spectrum, including red, green, and blue emissions, as well as specialty emissions, wherein the specialty emissions may include hyperspectral, fluorescence, or laser mapping emissions of electromagnetic energy. However, this disclosure does not indicate that the endoscope may be equipped with two or more image sensors for stereo visualization that are both disposed within an endoscope tube. Additionally, this disclosure does not indicate wherein the two or more image sensors may be equipped with different lenses, optical filters, pixel filters, and so forth for optimizing different types of visualization.

Consequently, a significant need exists for optimized lens assemblies for endoscopic stereo visualization of a scene. In view of the foregoing, described herein are systems, methods, and devices for stereo visualization with an endoscopic visualization system.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified.

Advantages of the disclosure will become better understood with regard to the following description and accompanying drawings where.

DETAILED DESCRIPTION

Figure 1A:
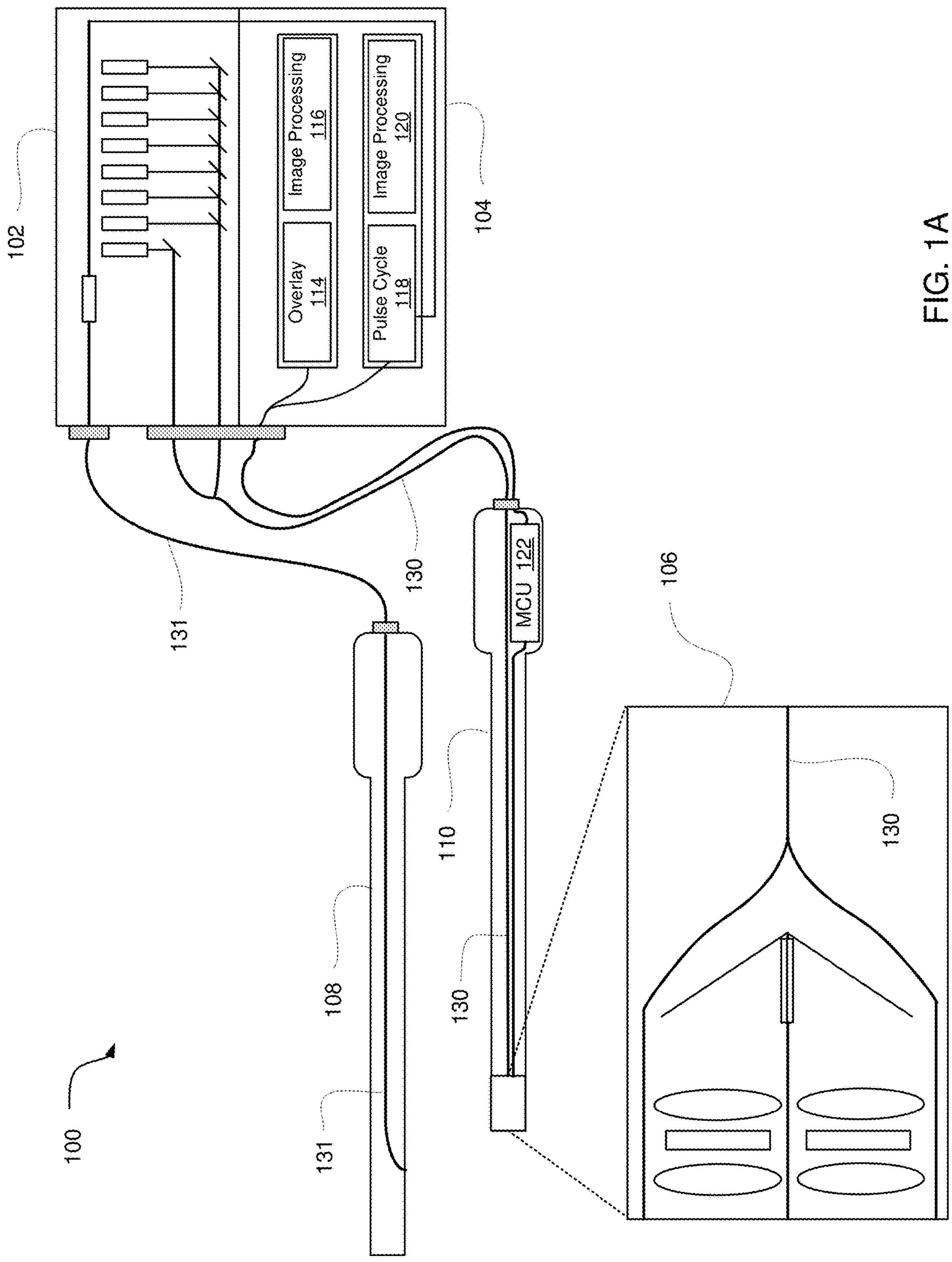
FIG. 1A is a schematic illustration of an example system for endoscopic visualization with color imaging and advanced imaging.

Disclosed herein are systems, methods, and devices for digital visualization that may be primarily suited to medical applications such as medical endoscopic imaging. Specifically disclosed herein are objective lens designs for an endoscopic visualization system that supports three-dimensional (i.e., stereo or stereoscopic) visualization of a scene utilizing two or more image sensors. The systems described herein include two or more image sensors disposed within an interior space defined by an endoscope tube.

For surgical endoscopes, and particularly those utilized in robotic surgery, it is beneficial to utilize an image acquisition head that supports three-dimensional visualization. However, it is difficult to disposed two or more image sensors, filters, and a lens assembly within the highly space constrained environment of an endoscope tube. In many cases, the endoscope tube has a diameter of less than 9 mm, and all visualization components must be disposed within this space. Further, numerous surgical tools are used in combination with a trocar and cannula assembly that can fit within an 8.7 mm outer diameter of the endoscope tube. In these cases, it can be necessary to ensure that the image sensors, filters, and lens assembly can all be disposed within an endoscope tube having a diameter of 8.7 mm or less. The objective lens assemblies described herein are designed to be disposed within a space-constrained environment and support three-dimensional visualization of a scene.

The objective lens assemblies described herein support high-resolution wide-field visualization to enable visualization of affected sites in a body cavity and medical treatment with high image quality. Additionally, the systems described herein are capable of providing fluorescence visualization data and/or multispectral visualization data in combination with color visualization data. The fluorescence visualization capabilities necessitate the inclusion of one or more filters that selectively block a fluorescence excitation waveband of electromagnetic radiation (EMR) and prevent the fluorescence excitation illumination from irradiating the image sensor. The objective lens assemblies described herein are configured to accommodate these filters.

An embodiment of the disclosure is an endoscopic system for color visualization and “advanced visualization” of a scene. The advanced visualization includes one or more of multispectral imaging, fluorescence imaging, or topographical mapping. Data retrieved from the advanced visualization may be processed by one or more algorithms configured to determine characteristics of the scene. The advanced visualization data may specifically be used to identify tissue structures within a scene, generate a three-dimensional topographical map of the scene, calculate dimensions of objects within the scene, identify margins and boundaries of different tissue types, and so forth.

An embodiment of the disclosure is an endoscopic visualization system that includes an emitter, an image sensor, and a controller. The emitter includes a plurality of separate and independently actuatable sources of electromagnetic radiation (“EMR”) that may be separately cycled on and off to illuminate a scene with pulses of EMR. The image sensor accumulates EMR and reads out data for generating a plurality of data frames. The controller synchronizes operations of the emitter and the image sensor to output a desired visualization scheme based on user input. The visualization scheme may include a selection of one or more of color imaging, multispectral imaging, fluorescence imaging, topographical mapping, or anatomical measurement.

The controller instructs the emitter and the image sensor to operate in a synchronized sequence to output a video stream that includes one or more types of visualization (i.e., color imaging, multispectral imaging, fluorescence imaging, topographical mapping, or anatomical measurement). The controller instructs the emitter to actuate one or more of the plurality of EMR sources to pulse according to a variable pulse cycle. The controller instructs the image sensor to accumulate EMR and read out data according to a variable sensor cycle that is synchronized in time with the variable pulse cycle. The synchronized sequence of the emitter and the image sensor enables the image sensor to read out data corresponding with a plurality of different visualization types. For example, the image sensor may read out a color frame in response to the emitter pulsing a white light or other visible EMR, the image sensor may readout a multispectral frame in response to the emitter pulsing a multispectral waveband of EMR, the image sensor may read out data for calculating a three-dimensional topographical map in response to the emitter pulsing EMR in a mapping pattern, and so forth.

The controller optimizes and adjusts a sensor cycle of an image sensor to output data frames for color imaging and/or advanced imaging at a sufficient rate, while ensuring the pixel array accumulates a sufficient amount of EMR for each data frame. The controller may instruct the image sensor to implement pixel binning on a per-frame basis, such that the image sensor implements pixel binning for some data frames and reads out all pixels for other data frames. In some cases, the controller instructs the image sensor to read out all pixels and thereby output a high-definition color data frame in response to the emitter pulsing white EMR. The controller may further instruct the image sensor to bin the pixel array and read out fewer pixels in response to the emitter pulsing EMR for advanced visualization, such as multispectral imaging, fluorescence imaging, or topographical mapping.

The controller may additionally optimize and adjust the variable pulse cycle in real-time based on user input, sufficient exposure of resultant data frames, and inherent properties of a corresponding pixel array. In some cases, a pixel array has varying sensitivities to different wavebands of EMR. In these cases, the pixel array is irradiated with EMR for shorter or longer durations of time depending on the type of illumination pulse to ensure the pixel array outputs data frames with consistent exposure levels. The controller adjusts the irradiation time of the pixel array and the pulsing duration of the emitter in real-time to compensate for the pixel array's varying efficiencies to different types of illumination.

The systems, methods, and devices described herein are implemented for color visualization and advanced visualization. The advanced visualization techniques described herein can be used to identify certain tissues, see through tissues in the foreground, calculate a three-dimensional topography of a scene, and calculate dimensions and distances for objects within the scene. The advanced visualization techniques described herein specifically include multispectral visualization, fluorescence visualization, and laser mapping visualization.

Multispectral Visualization

Spectral imaging uses multiple bands across the electromagnetic spectrum. This is different from conventional cameras that only capture light across the three wavelengths based in the visible spectrum that are discernable by the human eye, including the red, green, and blue wavelengths to generate an RGB image. Spectral imaging may use any wavelength bands in the electromagnetic spectrum, including infrared wavelengths, the visible spectrum, the ultraviolet spectrum, x-ray wavelengths, or any suitable combination of various wavelength bands. Spectral imaging may overlay imaging generated based on non-visible bands (e.g., infrared) on top of imaging based on visible bands (e.g., a standard RGB image) to provide additional information that is easily discernable by a person or computer algorithm.

The multispectral imaging techniques discussed herein can be used to "see through" layers of tissue in the foreground of a scene to identify specific types of tissue and/or specific biological or chemical processes. Multispectral imaging can be used in the medical context to quantitatively track the process of a disease and to determine tissue pathology. Additionally, multispectral imaging can be used to identify critical structures such as nerve tissue, muscle tissue, cancerous cells, blood vessels, and so forth. In an embodiment, multispectral partitions of EMR are pulsed and data is gathered regarding the spectral responses of different types of tissue in response to the partitions of EMR. A datastore of spectral responses can be generated and analyzed to assess a scene and predict which tissues are present within the scene based on the sensed spectral responses.

Multispectral imaging enables numerous advantages over conventional imaging. The information obtained by multispectral imaging enables medical practitioners and/or computer-implemented programs to precisely identify certain tissues or conditions that may not be possible to identify with RGB imaging. Additionally, multispectral imaging may be used during medical procedures to provide image-guided surgery that enables a medical practitioner to, for example, view tissues located behind certain tissues or fluids, identify atypical cancerous cells in contrast with typical healthy cells, identify certain tissues or conditions, identify critical structures, and so forth. Multispectral imaging provides specialized diagnostic information about tissue physiology, morphology, and composition that cannot be generated with conventional imaging.

Fluorescence Visualization

Fluorescence occurs when an orbital electron of a molecule, atom, or nanostructure is excited by light or other EMR, and then relaxes to its ground state by emitting a photon from the excited state. The specific frequencies of EMR that excite the orbital electron, or are emitted by the photon during relaxation, are dependent on the particular atom, molecule, or nanostructure. In most cases, the light emitted by the substance has a longer wavelength, and therefore lower energy, than the radiation that was absorbed by the substance.

Fluorescence imaging is particularly useful in biochemistry and medicine as a non-destructive means for tracking or analyzing biological molecules. The biological molecules, including certain tissues or structures, are tracked by analyzing the fluorescent emission of the biological molecules after being excited by a certain wavelength of EMR. However, relatively few cellular components are naturally fluorescent. In certain implementations, it may be desirable to visualize a certain tissue, structure, chemical process, or biological process that is not intrinsically fluorescent. In such an implementation, the body may be administered a dye or reagent that may include a molecule, protein, or quantum dot having fluorescent properties. The reagent or dye may then fluoresce after being excited by a certain wavelength of EMR. Different reagents or dyes may include different molecules, proteins, and/or quantum dots that will fluoresce at particular wavelengths of EMR. Thus, it may be necessary to excite the reagent or dye with a specialized band of EMR to achieve fluorescence and identify the desired tissue, structure, or process in the body.

The fluorescence imaging techniques described herein may be used to identify certain materials, tissues, components, or processes within a body cavity or other light deficient environment. Fluorescence imaging data may be provided to a medical practitioner or computer-implemented algorithm to enable the identification of certain structures or tissues within a body. Such fluorescence imaging data may be overlaid on black-and-white or RGB images to provide additional information and context.

The fluorescence imaging techniques described herein may be implemented in coordination with fluorescent reagents or dyes. Some reagents or dyes are known to attach to certain types of tissues and fluoresce at specific wavelengths of the electromagnetic spectrum. In an implementation, a reagent or dye is administered to a patient that is configured to fluoresce when activated by certain wavelengths of light. The visualization system disclosed herein is used to excite and fluoresce the reagent or dye. The fluorescence of the reagent or dye is detected by an image sensor to aid in the identification of tissues or structures in the body cavity. In an implementation, a patient is administered a plurality of reagents or dyes that are each configured to fluoresce at different wavelengths and/or provide an indication of different structures, tissues, chemical reactions, biological processes, and so forth. In such an implementation, the visualization system described herein emits each of the applicable wavelengths to fluoresce each of the applicable reagents or dyes. This may negate the need to perform individual imaging procedures for each of the plurality of reagents or dyes.

Laser Mapping Visualization

Laser mapping generally includes the controlled deflection of laser beams. Laser mapping can be implemented to generate one or more of a three-dimensional topographical map of a scene, calculate distances between objects within the scene, calculate dimensions of objects within the scene, track the relative locations of tools within the scene, and so forth.

Laser mapping combines controlled steering of laser beams with a laser rangefinder. By taking a distance measurement at every direction, the laser rangefinder can rapidly capture the surface shape of objects, tools, and landscapes. Construction of a full three-dimensional topography may include combining multiple surface models that are obtained from different viewing angles. Various measurement systems and methods exist in the art for applications in archaeology, geography, atmospheric physics, autonomous vehicles, and others. One such system includes light detection and ranging (LIDAR), which is a three-dimensional mapping system. LIDAR has been applied in navigation systems such as airplanes or satellites to determine position and orientation of a sensor in combination with other systems and sensors. LIDAR uses active sensors to illuminate an object and detect energy that is reflected off the object and back to a sensor.

As discussed herein, the term "laser mapping" includes laser tracking. Laser tracking, or the use of lasers for tool tracking, measures objects by determining the positions of optical targets held against those objects. Laser trackers can be accurate to the order of 0.025 mm over a distance of several meters. The visualization system described herein pulses EMR for use in conjunction with a laser tracking system such that the position of tools within a scene can be tracked and measured.

The endoscopic visualization system described herein implements laser mapping imaging to determine precise measurements and topographical outlines of a scene. In one implementation, mapping data is used to determine precise measurements between, for example, structures or organs in a body cavity, devices, or tools in the body cavity, and/or critical structures in the body cavity. As discussed herein, the term "mapping" encompasses technologies referred to as laser mapping, laser scanning, topographical scanning, three-dimensional scanning, laser tracking, tool tracking, and others. A mapping data frame as discussed herein includes data for calculating one or more of a topographical map of a scene, dimensions of objects or structures within a scene, distances between objects or structures within the scene, relative locations of tools or other objects within the scene, and so forth.

Additionally, the systems described herein are capable of calculating a disparity map for generating a three-dimensional rendering of a scene. Disparity is the apparent motion of objects between a pair of stereo images. Given a pair of stereo images, the disparity map is computed by matching each pixel within the "left image" with its corresponding pixel within the "right image." Then, the distance is computed for each pair of matching pixel. Finally, the disparity map is generated by representing these distance values as an intensity image. The depth is inversely proportional to the disparity, and thus, when the geometric arrangement of the image sensors is known, the disparity map is converted into a depth map using triangulation.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems, and methods are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a farthest portion, depending upon the context.

As used herein, color sensors are sensors known to have a color filter array (CFA) thereon to filter the incoming EMR into its separate components. In the visual range of the electromagnetic spectrum, such a CFA may be built on a Bayer pattern or modification thereon to separate green, red, and blue spectrum components of visible EMR.

As used herein, a monochromatic sensor refers to an unfiltered imaging sensor comprising color-agnostic pixels.

The systems, methods, and devices described herein are specifically optimized to account for variations between "stronger" electromagnetic radiation (EMR) sources and "weaker" EMR sources. In some cases, the stronger EMR sources are considered "stronger" based on the inherent qualities of a pixel array, e.g., if a pixel array is inherently more sensitive to detecting EMR emitted by the stronger EMR source, then the stronger EMR source may be classified as "stronger" when compared with another EMR source. Conversely, if the pixel array is inherently less sensitive to detecting EMR emitted by the weaker EMR source, then the weaker EMR source may be classified as "weaker" when compared with another EMR source. Additionally, a "stronger" EMR source may have a higher amplitude, greater brightness, or higher energy output when compared with a "weaker" EMR source. The present disclosure addresses the disparity between stronger EMR sources and weaker EMR sources by adjusting a pulse cycle of an emitter to ensure a pixel array has sufficient time to accumulate a sufficient amount of EMR corresponding with each of a stronger EMR source and a weaker EMR source.

Figure 1B:
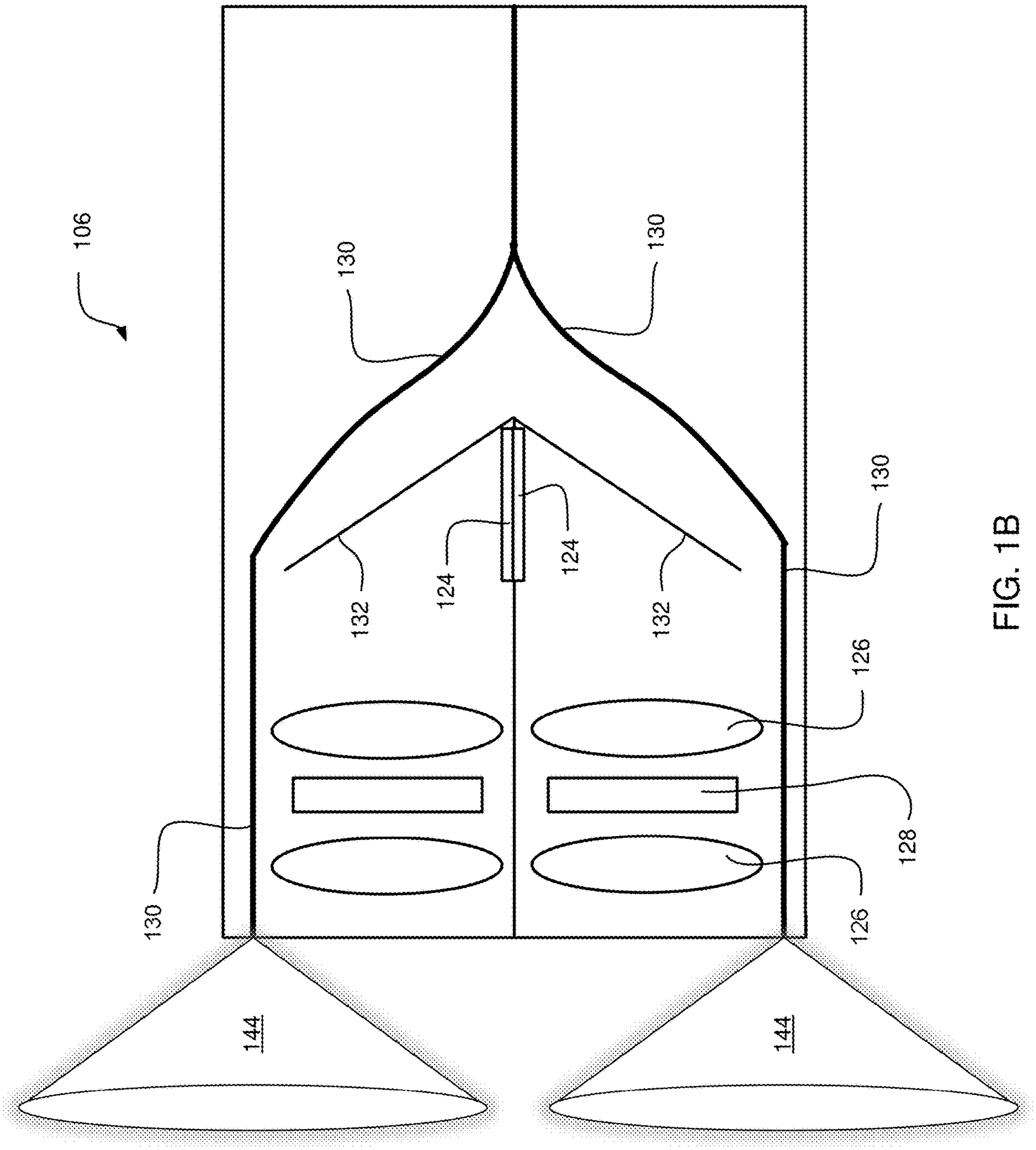
FIG. 1B is a schematic illustration of an example image pickup portion of a system for endoscopic visualization with color imaging and advanced imaging.
Figure 1C:
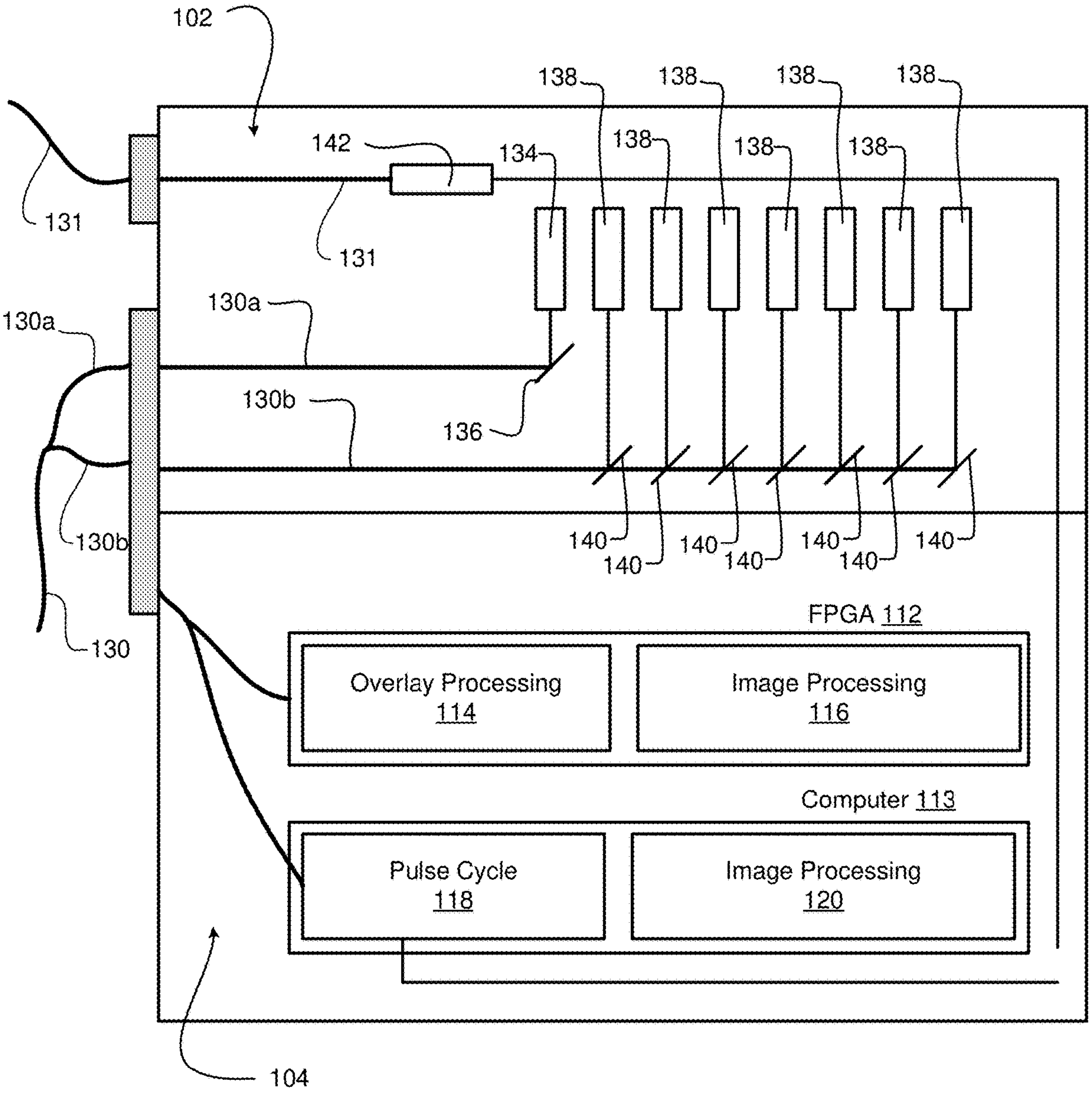
FIG. 1C is a schematic illustration of an example emitter and controller of a system for endoscopic visualization with color imaging and advanced imaging.

Referring now to the figures, FIGS. 1A-1C illustrate schematic diagrams of a system 100 for endoscopic visualization. The system 100 includes an emitter 102, a controller 104, and an optical visualization system 106. The system 100 includes one or more tools 108, which may include endoscopic tools such as forceps, brushes, scissors, cutters, burs, staplers, ligation devices, tissue staplers, suturing systems, and so forth. The system 100 includes one or more endoscopes 110 such as arthroscopes, bronchoscopes, colonoscopes, colposcopes, cystoscopes, esophagoscope, gastroscopes, laparoscopes, laryngoscopes, neuroendoscopes, proctoscopes, sigmoidoscopes, thoracoscopes, and so forth. The system 100 may include additional endoscopes 110 and/or tools 108 with an image sensor equipped therein. In these implementations, the system 100 is equipped to output stereo visualization data for generating a three-dimensional topographical map of a scene using disparity mapping and triangulation.

The optical visualization system 106 may be disposed at a distal end of a tube of an endoscope 110. Alternatively, one or more components of the optical visualization system 106 may be disposed at a proximal end of the tube of the endoscope 110 or in another region of the endoscope 110. The optical visualization system 106 includes components for directing beams of EMR on to the pixel array 125 of the one or more image sensors 124. The optical visualization system 106 may include any of the lens assembly components described herein.

Figure 2A:
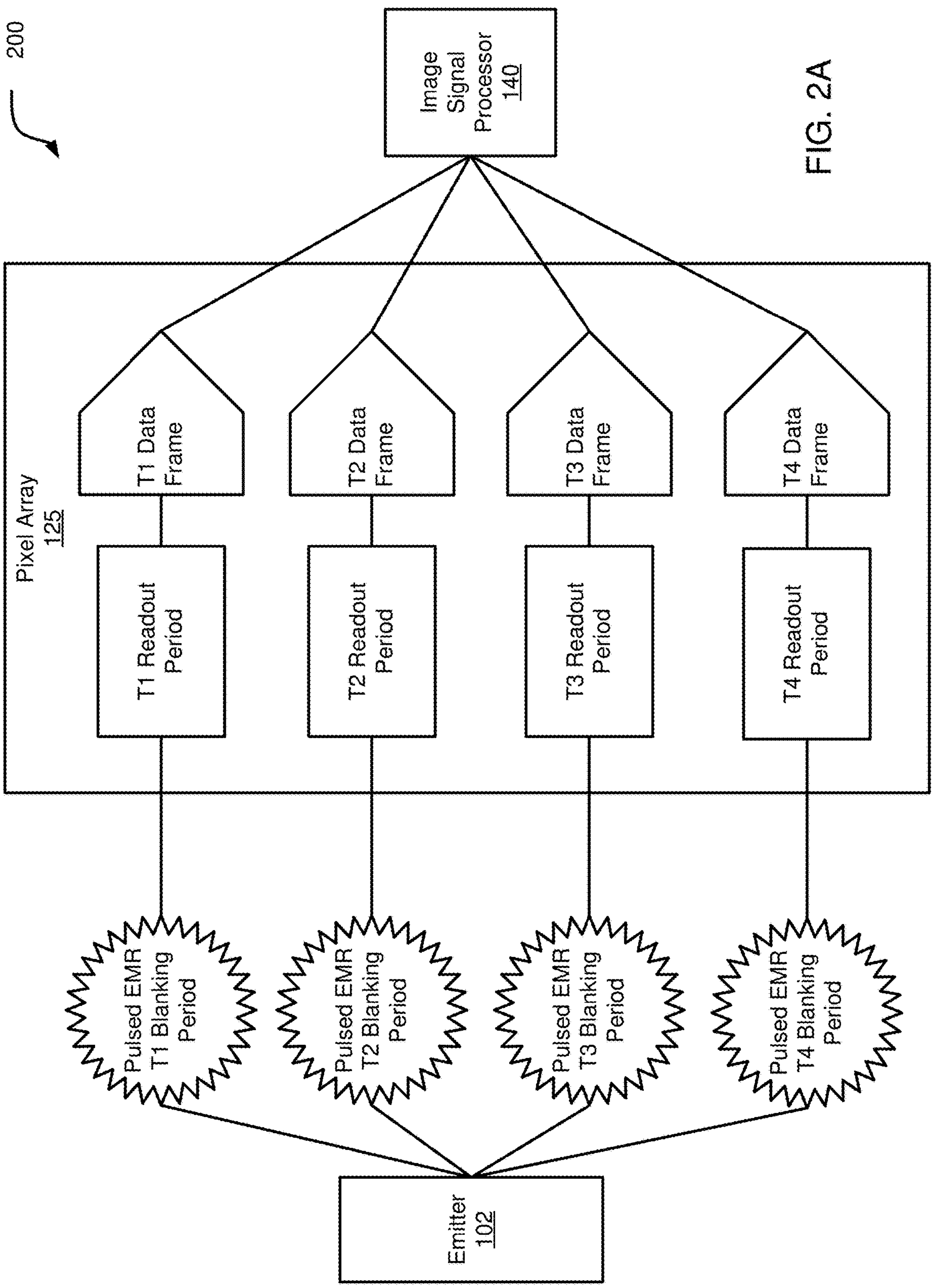
FIG. 2A is a schematic block diagram of an example data flow for a time-sequenced visualization system.

The optical visualization system 106 may include one or more image sensors 124 that each include a pixel array (see pixel array 125 first illustrated in FIG. 2A). The optical visualization system 106 may include one or more lenses 126 and filters 128 and may further include one or more prisms 132 for reflecting EMR on to the pixel array 125 of the one or more image sensors 124. The system 100 may include a waveguide 130 configured to transmit EMR from the emitter 102 to a distal end of the endoscope 110 to illuminate a light deficient environment for visualization, such as within a surgical scene. The system 100 may further include a waveguide 131 configured to transmit EMR from the emitter 102 to a termination point on the tool 108, which may specifically be actuated for laser mapping imaging and tool tracking as described herein.

The optical visualization system 106 may specifically include two lenses 126 dedicated to each image sensor 124 to focus EMR on to a rotated image sensor 124 and enable a depth view. The filter 128 may include a notch filter configured to block unwanted reflected EMR. In a particular use-case, the unwanted reflected EMR may include a fluorescence excitation wavelength that was pulsed by the emitter 102, wherein the system 100 wishes to only detect a fluorescence relaxation wavelength emitted by a fluorescent reagent or tissue.

The optical visualization system 106 may additionally include an inertial measurement unit (IMU) (not shown). The IMU may be configured to track the real-time movements and rotations of the image sensor 124. Sensor data output from the IMU may be provided to the controller 104 to improve post processing of image frames output by the image sensor 124. Specifically, sensor data captured by the IMU may be utilized to stabilize the movement of image frames and/or the movement of false color overlays rendered over color image frames.

The image sensor 124 includes one or more image sensors, and the example implementation illustrated in FIGS. 1A-1B illustrates an optical visualization system 106 comprising two image sensors 124. The image sensor 124 may include a CMOS image sensor and may specifically include a high-resolution image sensor configured to read out data according to a rolling readout scheme. The image sensors 124 may include a plurality of different image sensors that are tuned to collect different wavebands of EMR with varying efficiencies. In an implementation, the image sensors 124 include separate image sensors that are optimized for color imaging, fluorescence imaging, multispectral imaging, and/or topographical mapping.

The optical visualization system 106 typically includes multiple image sensors 124 such that the system 100 is equipped to output stereo visualization data. In some cases, stereo data frames are assessed to output a disparity map showing apparent motion of objects between the "left" stereo image and the "right" stereo image. Because the geographical locations of the image sensors 124 is known, the disparity map may then be used to generate a three-dimensional topographical map of a scene using triangulation.

The emitter 102 includes one or more EMR sources, which may include, for example, lasers, laser bundles, light emitting diodes (LEDs), electric discharge sources, incandescence sources, electroluminescence sources, and so forth. In some implementations, the emitter 102 includes at least one white EMR source 134 (may be referred to herein as a white light source). The emitter 102 may additionally include one or more EMR sources 138 that are tuned to emit a certain waveband of EMR. The EMR sources 138 may specifically be tuned to emit a waveband of EMR that is selected for multispectral or fluorescence visualization. The emitter 102 may additionally include one or more mapping sources 142 that are configured to emit EMR in a mapping pattern such as a grid array or dot array selected for capturing data for topographical mapping or anatomical measurement.

The one or more white EMR sources 134 emit EMR into a dichroic mirror 136 that feeds the white EMR into a waveguide 130, which may specifically include a fiber optic cable or other means for carrying EMR to the endoscope. The white EMR source 134 may specifically feed into a first waveguide **130*a* dedicated to white EMR. The EMR sources 138 emit EMR into independent dichroic mirrors 140 that each feed EMR into the waveguide 130 and may specifically feed into a second waveguide 130*b*. The first waveguide 130*a* and the second waveguide 130*b* later merge into a waveguide 130 that transmits EMR to a distal end of the endoscope 110 to illuminate a scene with an emission of EMR 144**.

The one or more EMR sources 138 that are tuned to emit a waveband of EMR may specifically be tuned to emit EMR that is selected for multispectral or fluorescence visualization. In some cases, the EMR sources 138 are finely tuned to emit a central wavelength of EMR with a tolerance threshold not exceeding ±5 nm, ±4 nm, ±3 nm, ±2 nm, or ±1 nm. The EMR sources 138 may include lasers or laser bundles that are separately cycled on and off by the emitter 102 to pulse the emission of EMR 144 and illuminate a scene with a finely tuned waveband of EMR.

The one or more mapping sources 142 are configured to pulse EMR in a mapping pattern, which may include a dot array, grid array, vertical hashing, horizontal hashing, pin grid array, and so forth. The mapping pattern is selected for laser mapping imaging to determine one or more of a three-dimensional topographical map of a scene, a distance between two or more objects within a scene, a dimension of an object within a scene, a location of a tool 108 within the scene, and so forth. The EMR pulsed by the mapping source 142 is diffracted to spread the energy waves according to the desired mapping pattern. The mapping source 142 may specifically include a device that splits the EMR beam with quantum-dot-array diffraction grafting. The mapping source 142 may be configured to emit low mode laser light.

The controller 104 (may be referred to herein as a camera control unit or CCU) may include a field programmable gate array (FGPA) 112 and a computer 113. The FGPA 112 may be configured to perform overlay processing 114 and image processing 116. The computer 113 may be configured to generate a pulse cycle 118 for the emitter 102 and to perform further image processing 120. The FGPA 112 receives data from the image sensor 124 and may combine data from two or more data frames by way of overlay processing 114 to output an overlay image frame. The computer 113 may provide data to the emitter 102 and the image sensor 124. Specifically, the computer 113 may calculate and adjust a variable pulse cycle to be emitted by the emitter 102 in real-time based on user input. Additionally, the computer 113 may receive data frames from the image sensor 124 and perform further image processing 120 on those data frames.

The controller 104 may be in communication with a network, such as the Internet, and automatically upload data to the network for remote storage. The MCU 122 and image sensors 124 may be exchanged and updated and continue to communicate with an established controller 104. In some cases, the controller 104 is "out of date" with respect to the MCU 122 but will still successfully communicate with the MCU 122. This may increase the data security for a hospital or other healthcare facility because the existing controller 104 may be configured to undergo extensive security protocols to protect patient data.

The controller 104 may communicate with a microcontroller unit (MCU) 122 disposed within a handpiece of the endoscope and/or the image sensor 124 by way of a data transmission pipeline 146. The data transmission pipeline 146 may include a data connection port disposed within a housing of the emitter 102 or the controller 104 that enables a corresponding data cable to carry data to the endoscope 110. In another embodiment, the controller 104 wirelessly communicates with the MCU 122 and/or the image sensor 124 to provide instructions for upcoming data frames. One frame period includes a blanking period and a readout period. Generally speaking, the pixel array 125 accumulates EMR during the blanking period and reads out pixel data during the readout period. It will be understood that a blanking period corresponds to a time between a readout of a last row of active pixels in the pixel array of the image sensor and a beginning of a next subsequent readout of active pixels in the pixel array. Additionally, the readout period corresponds to a duration of time when active pixels in the pixel array are being read. Further, the controller 104 may write correct registers to the image sensor 124 to adjust the duration of one or more of the blanking period or the readout period for each frame period on a frame-by-frame basis within the sensor cycle as needed.

The controller 104 may reprogram the image sensor 124 for each data frame to set a required blanking period duration and/or readout period duration for a subsequent frame period. In some cases, the controller 104 reprograms the image sensor 124 by first sending information to the MCU 122, and then the MCU 122 communicates directly with the image sensor 124 to rewrite registers on the image sensor 124 for an upcoming data frame.

The MCU 122 may be disposed within a handpiece portion of the endoscope 110 and communicate with electronic circuitry (such as the image sensor 124) disposed within a distal end of a tube of the endoscope 110. The MCU 122 receives instructions from the controller 104, including an indication of the pulse cycle 118 provided to the emitter 102 and the corresponding sensor cycle timing for the image sensor 124. The MCU 122 executes a common Application Program Interface (API). The controller 104 communicates with the MCU 122, and the MCU 122 executes a translation function that translates instructions received from the controller 104 into the correct format for each type of image sensor 124. In some cases, the system 100 may include multiple different image sensors that each operate according to a different "language" or formatting, and the MCU 122 is configured to translate instructions from the controller 104 into each of the appropriate data formatting languages. The common API on the MCU 122 passes information by the scene, including, for example parameters pertaining to gain, exposure, white balance, setpoint, and so forth. The MCU 122 runs a feedback algorithm to the controller 104 for any number of parameters depending on the type of visualization.

The MCU 122 stores operational data and images captured by the image sensors 124. In some cases, the MCU 122 does not need to continuously push data up the data chain to the controller 104. The data may be set once on the microcontroller 122, and then only critical information may be pushed through a feedback loop to the controller 104. The MCU 122 may be set up in multiple modes, including a primary mode (may be referred to as a "master" mode when referring to a master/slave communication protocol). The MCU 122 ensures that all downstream components (i.e., distal components including the image sensors 124, which may be referred to as "slaves" in the master/slave communication protocol) are apprised of the configurations for upcoming data frames. The upcoming configurations may include, for example, gain, exposure duration, readout duration, pixel binning configuration, and so forth.

The MCU 122 includes internal logic for executing triggers to coordinate different devices, including, for example multiple image sensors 124. The MCU 122 provides instructions for upcoming frames and executes triggers to ensure that each image sensor 124 begins to capture data the same time. In some cases, the image sensors 124 may automatically advance to a subsequent data frame without receiving a unique trigger from the MCU 122.

In some cases, the endoscope 110 includes two or more image sensors 124 that detect EMR and output data frames simultaneously. The simultaneous data frames may be used to output a three-dimensional image and/or output imagery with increased definition and dynamic range. The pixel array of the image sensor 124 may include active pixels and optical black ("OB") or optically blind pixels. The optical black pixels may be read during a blanking period of the pixel array when the pixel array is "reset" or calibrated. After the optical black pixels have been read, the active pixels are read during a readout period of the pixel array. The active pixels accumulate EMR that is pulsed by the emitter 102 during the blanking period of the image sensor 124. The pixel array 125 may include monochromatic or "color agnostic" pixels that do not comprise any filter for selectively receiving certain wavebands of EMR. The pixel array may include a color filter array (CFA), such as a Bayer pattern CFA, that selectively allows certain wavebands of EMR to pass through the filters and be accumulated by the pixel array.

The image sensor 124 is instructed by a combination of the MCU 122 and the controller 104 working in a coordinated effort. Ultimately, the MCU 122 provides the image sensor 124 with instructions on how to capture the upcoming data frame. These instructions include, for example, an indication of the gain, exposure, white balance, exposure duration, readout duration, pixel binning configuration, and so forth for the upcoming data frame. When the image sensor 124 is reading out data for a current data frame, the MCU 122 is rewriting the correct registers for the next data frame. The MCU 122 and the image sensor 124 operate in a back-and-forth data flow, wherein the image sensor 124 provides data to the MCU 122 and the MCU 122 rewrites correct registers to the image sensor 124 for each upcoming data frame. The MCU 122 and the image sensor 124 may operate according to a "ping pong buffer" in some configurations.

The image sensor 124, MCU 122, and controller 104 engage in a feedback loop to continuously adjust and optimize configurations for upcoming data frames based on output data. The MCU 122 continually rewrites correct registers to the image sensor 124 depending on the type of upcoming data frame (i.e., color data frame, multispectral data frame, fluorescence data frame, topographical mapping data frame, and so forth), configurations for previously output data frames, and user input. In an example implementation, the image sensor 124 outputs a multispectral data frame in response to the emitter 102 pulsing a multispectral waveband of EMR. The MCU 122 and/or controller 104 determines that the multispectral data frame is underexposed and cannot successfully be analyzed by a corresponding machine learning algorithm. The MCU 122 and/or controller 104 than adjusts configurations for upcoming multispectral data frames to ensure that future multispectral data frames are properly exposed. The MCU 122 and/or controller 104 may indicate that the gain, exposure duration, pixel binning configuration, etc. must be adjusted for future multispectral data frames to ensure proper exposure. All image sensor 124 configurations may be adjusted in real-time based on previously output data processed through the feedback loop, and further based on user input.

The waveguides 130, 131 include one or more optical fibers. The optical fibers may be made of a low-cost material, such as plastic to allow for disposal of one or more of the waveguides 130, 131. In some implementations, one or more of the waveguides 130, 131 include a single glass fiber having a diameter of 500 microns. In some implementations, one or more of the waveguides 130, 131 include a plurality of glass fibers.

Figure 2B:
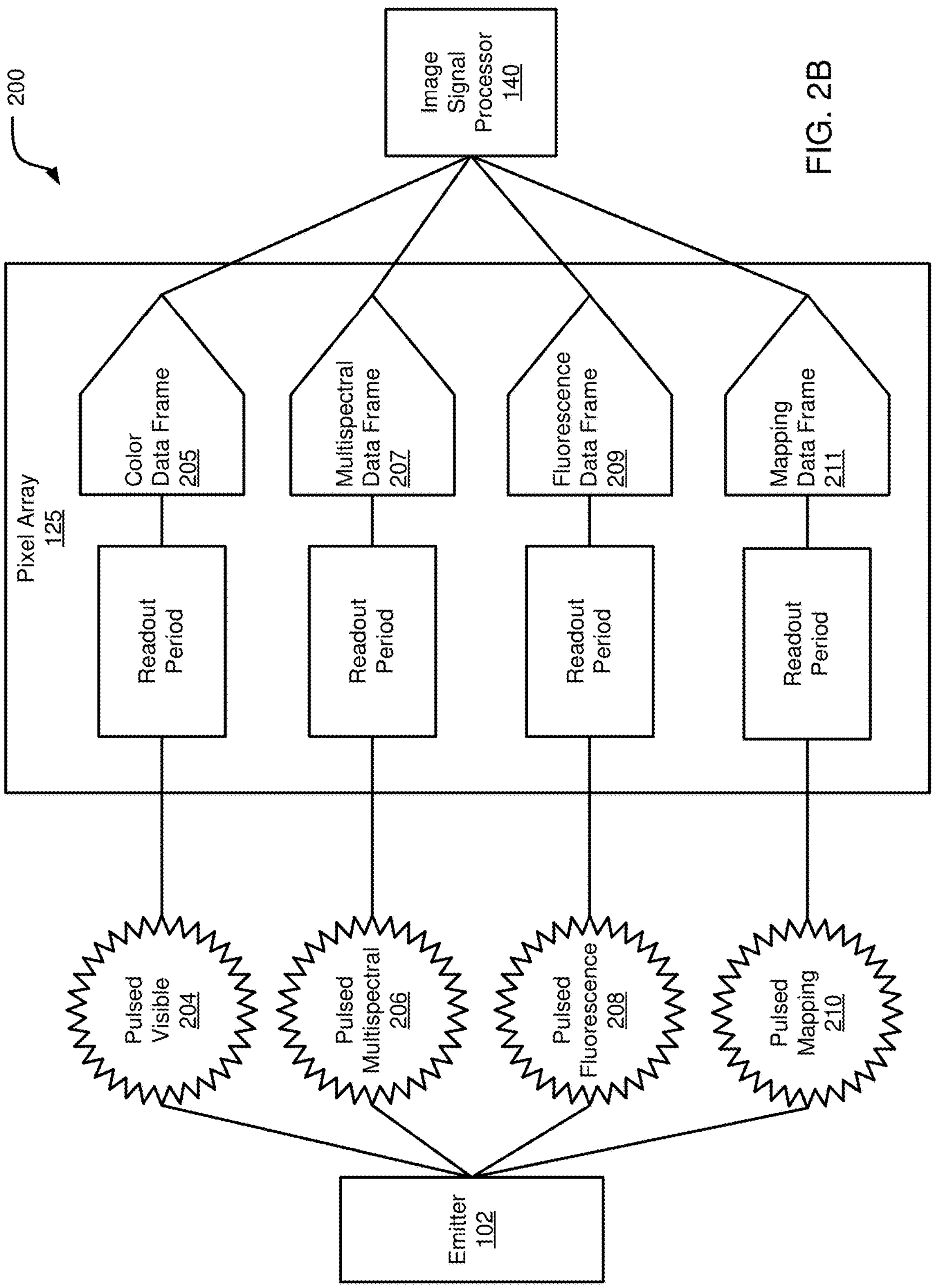
FIG. 2B is a schematic block diagram of an example data flow for a time-sequenced visualization system.

FIGS. 2A and 2B each illustrate a schematic diagram of a data flow 200 for time-sequenced visualization of a light deficient environment. The data flow 200 illustrated in FIGS. 2A-2B may be implemented by the system 100 for endoscopic visualization illustrated in FIGS. 1A-1C. FIG. 2A illustrates a generic implementation that may be applied to any type of illumination or wavelengths of EMR. FIG. 2B illustrates an example implementation wherein the emitter 102 actuates visible, multispectral, fluorescence, and mapping EMR sources.

The data flow 200 includes an emitter 102, a pixel array 125 of an image sensor 124 (not shown), and an image signal processor 140. The image signal processor 140 may include one or more of the image processing 116, 120 modules illustrated in FIGS. 1A and 1C. The emitter 102 includes a plurality of separate and independently actuatable EMR sources (see, e.g., 134, 138 illustrated in FIGS. 1A and 1C). Each of the EMR sources can be cycled on and off to emit a pulse of EMR with a defined duration and magnitude. The pixel array 125 of the image sensor 124 may include a color filter array (CFA) or an unfiltered array comprising color-agnostic pixels. The emitter 102 and the pixel array 125 are each in communication with a controller 104 (not shown in FIGS. 2A-2B) that instructs the emitter 102 and the pixel array 125 to synchronize operations to generate a plurality of data frames according to a desired visualization scheme.

The controller 104 instructs the emitter 102 to cycle the plurality of EMR sources according to a variable pulse cycle. The controller 104 calculates the variable pulse cycle based at least in part upon a user input indicating the desired visualization scheme. For example, the desired visualization scheme may indicate the user wishes to view a scene with only color imaging. In this case, the variable pulse cycle may include only pulses of white EMR. In an alternative example, the desired visualization scheme may indicate the user wishes to be notified when nerve tissue can be identified in the scene and/or when a tool within the scene is within a threshold distance from the nerve tissue. In this example, the variable pulse cycle may include pulses of white EMR and may further include pulses of one or more multispectral wavebands of EMR that elicit a spectral response from the nerve tissue and/or "see through" non-nerve tissues by penetrating those non-nerve tissues. Additionally, the variable pulse cycle may include pulses of EMR in a mapping pattern configured for laser mapping imaging to determine when the tool is within the threshold distance from the nerve tissue. The controller 104 may reconfigure the variable pulse cycle in real-time in response to receiving a revised desired visualization scheme from the user.

FIG. 2A illustrates wherein the emitter cycles one or more EMR sources on and off to emit a pulse of EMR during each of a plurality of separate blanking periods of the pixel array 125. Specifically, the emitter 102 emits pulsed EMR during each of a T1 blanking period, T2 blanking period, T3 blanking period, and T4 blanking period of the pixel array 125. The pixel array 125 accumulates EMR during its blanking periods and reads out data during its readout periods.

Specifically, the pixel array 125 accumulates EMR during the T1 blanking period and reads out the T1 data frame during the T1 readout period, which follows the T1 blanking period. Similarly, the pixel array 125 accumulates EMR during the T2 blanking period and reads out the T2 data frame during the T2 readout period, which follows the T2 blanking period. The pixel array 125 accumulates EMR during the T3 blanking period and reads out the T3 data frame during the T3 readout period, which follows the T3 blanking period. The pixel array 125 accumulates EMR during the T4 blanking period and reads out the T4 data frame during the T4 readout period, which follows the T4 blanking period. Each of the T1 data frame, the T2 data frame, the T3 data frame, and the T4 data frame is provided to the image signal processor 140.

The contents of each of the T1-T4 data frames is dependent on the type of EMR that was pulsed by the emitter 102 during the preceding blanking period. For example, if the emitter 102 pulses white light during the preceding blanking period, then the resultant data frame may include a color data frame (if the pixel array 125 includes a color filter array for outputting red, green, and blue image data). Further for example, if the emitter 102 pulses a multispectral waveband of EMR during the preceding blanking period, then the resultant data frame is a multispectral data frame comprising information for identifying a spectral response by one or more objects within the scene and/or information for "seeing through" one or more structures within the scene. Further for example, if the emitter 102 pulses a fluorescence excitation waveband of EMR during the preceding blanking period, then the resultant data frame is a fluorescence data frame comprising information for identifying a fluorescent reagent or autofluorescence response by a tissue within the scene. Further for example, if the emitter 102 pulses EMR in a mapping pattern during the preceding blanking period, then the resultant data frame is a mapping data frame comprising information for calculating one or more of a three-dimensional topographical map of the scene, a dimension of one or more objects within the scene, a distance between two or more objects within the scene, and so forth.

Some "machine vision" or "computer vision" data frames, including multispectral data frames, fluorescence data frames, and mapping data frames may be provided to a corresponding algorithm or neural network configured to evaluate the information therein. A multispectral algorithm may be configured to identify one or more tissue structures within a scene based on how those tissue structures respond to one or more different wavebands of EMR selected for multispectral imaging. A fluorescence algorithm may be configured to identify a location of a fluorescent reagent or auto-fluorescing tissue structure within a scene. A mapping algorithm may be configured to calculate one or more of a three-dimensional topographical map of a scene, a depth map, a dimension of one or more objects within the scene, and/or a distance between two or more objects within the scene based on the mapping data frame.

FIG. 2B illustrates an example wherein the emitter 102 cycles separate visible, multispectral, fluorescence, and mapping EMR sources to emit pulsed visible 204, pulsed multispectral 206, pulsed fluorescence 208, and pulsed EMR in a mapping pattern 210. It should be appreciated that FIG. 2B is illustrative only, and that the emissions 204, 206, 208, 210 may be emitted in any order, may be emitted during a single visualization session as shown in FIG. 2B, and may be emitted during separate visualization sessions.

The pixel array 125 reads out a color data frame 205 in response to the emitter 102 pulsing the pulsed visible 204 EMR. The pulsed visible 204 EMR may specifically include a pulse of white light. The pixel array 125 reads out a multispectral data frame 207 in response to the emitter 102 pulsing the multispectral 206 waveband of EMR. The pulsed multispectral 206 waveband of EMR may specifically include one or more of EMR within a waveband from about 513-545 nanometers (nm), 565-585 nm, 770-790 nm, and/or 900-1000 nm. It will be appreciated that the pulsed multispectral 206 waveband of EMR may include various other wavebands used to elicit a spectral response. The pixel array 125 reads out a fluorescence data frame 209 in response to the emitter 102 pulsing the fluorescence 208 waveband of EMR. The pulsed fluorescence 208 waveband of EMR may specifically include one or more of EMR within a waveband from about 770-795 nm and/or 790-815 nm. The pixel array 125 reads out a mapping data frame 211 in response to the emitter 102 pulsing EMR in a mapping pattern 210. The pulsed mapping pattern 210 may include one or more of vertical hashing, horizontal hashing, a pin grid array, a dot array, a raster grid of discrete points, and so forth. Each of the color data frame 205, the multispectral data frame 207, the fluorescence data frame 209, and the mapping data frame 211 is provided to the image signal processor 140.

In an implementation, the emitter 102 separately pulses red, green, and blue visible EMR. In this implementation, the pixel array 125 may include a monochromatic (color agnostic) array of pixels. The pixel array 125 may separately read out a red data frame, a green data frame, and a blue data frame in response to the separate pulses of red, green, and blue visible EMR.

In an implementation, the emitter 102 separately pulses wavebands of visible EMR that are selected for capturing luminance ("Y") imaging data, red chrominance ("Cr") imaging data, and blue chrominance ("Cb") imaging data. In this implementation, the pixel array 125 may separately read out a luminance data frame (comprising only luminance imaging information), a red chrominance data frame, and a blue chrominance data frame.

Figure 2C:
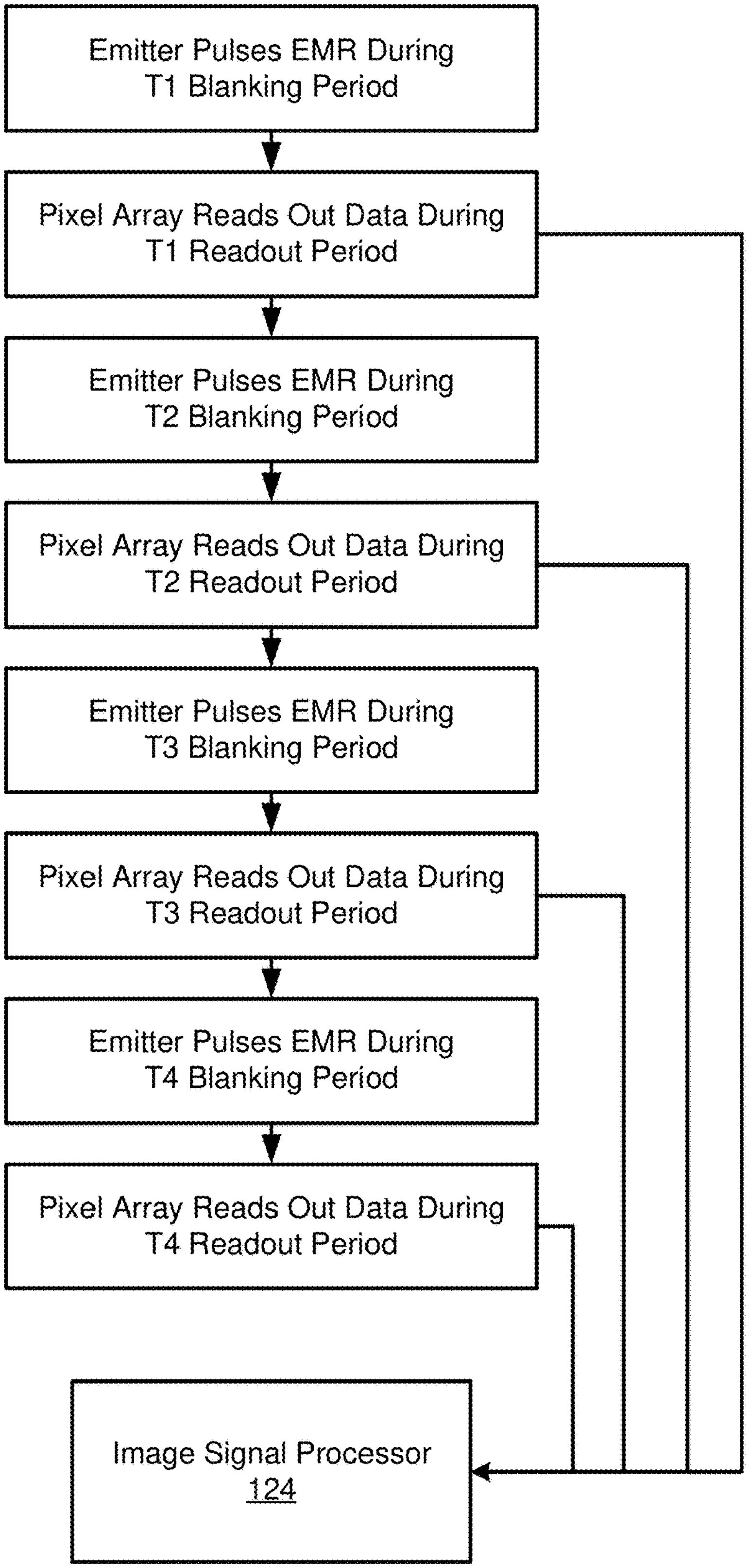
FIG. 2C is a schematic flow chart diagram of a data flow for capturing and reading out data for a time-sequenced visualization system.

FIG. 2C illustrates a schematic flow chart diagram of a process flow for synchronizing operations of the emitter 102 and the pixel array 125. The process flow corresponds with the schematic diagram illustrated in FIG. 2A. The process flow includes the controller 104 instructing the emitter 102 to pulse EMR during a T1 blanking period of the pixel array 125 and then instructing the pixel array 125 to read out data during a T1 readout period following the T1 blanking period. Similarly, the controller 104 instructs the emitter to pulse EMR during each of the T2 blanking period, the T3 blanking period, and the T4 blanking period. The controller 104 instructs the emitter to read out data during each of the T2 readout period, the T3 readout period, and the T4 readout period that follow the corresponding blanking periods. Each of the output data frames are provided to the image signal processor 140.

The emitter 102 pulses according to a variable pulse cycle that includes one or more types of EMR. The variable pulse cycle may include visible EMR, which may include a white light emission, red light emission, green light emission, blue light emission, or some other waveband of visible EMR. The white light emission may be pulsed with a white light emitting diode (LED) or other light source and may alternatively be pulsed with a combination of red, green, and blue light sources pulsing in concert. The variable pulse cycle may include one or more wavebands of EMR that are selected for multispectral imaging or fluorescence imaging. The variable pulse cycle may include one or more emissions of EMR in a mapping pattern selected for three-dimensional topographical mapping or calculating dimensions within a scene. In some cases, several types of EMR are represented in the variable pulse cycle with different regularity than other types of EMR. This may be implemented to emphasize and de-emphasize aspects of the recorded scene as desired by the user.

The controller 104 adjusts the variable pulse cycle in real-time based on the visualization objectives. The system enables a user to input one or more visualization objectives and to change those objectives while using the system. For example, the visualization objective may indicate the user wishes to view only color imaging data, and in this case, the variable pulse cycle may include pulsed or constant emissions of white light (or other visible EMR). The visualization objective may indicate the user wishes to be notified when a scene includes one or more types of tissue or conditions that may be identified using one or more of color imaging, multispectral imaging, or fluorescence imaging. The visualization objective may indicate that a patient has been administered a certain fluorescent reagent or dye, and that fluorescence imaging should continue while the reagent or dye remains active. The visualization objective may indicate the user wishes to view a three-dimensional topographical map of a scene, receive information regarding distances or dimensions within the scene, receive an alert when a tool comes within critical distance from a certain tissue structure, and so forth.

The variable pulse cycle may include one or more finely tuned partitions of the electromagnetic spectrum that are selected to elicit a fluorescence response from a reagent, dye, or auto-fluorescing tissue. The fluorescence excitation wavebands of EMR include one or more of the following: 400±50 nm, 450±50 nm, 500±50 nm, 550±50 nm, 600±50 nm, 650±50 nm, 700±50 nm, 710±50 nm, 720±50 nm, 730±50 nm, 740±50 nm, 750±50 nm, 760±50 nm, 770±50 nm, 780±50 nm, 790±50 nm, 800±50 nm, 810±50 nm, 820±50 nm, 830±50 nm, 840±50 nm, 850±50 nm, 860±50 nm, 870±50 nm, 880±50 nm, 890±50 nm, or 900±50 nm. The aforementioned wavebands may be finely tuned such that the emitter pulses the central wavelength with a tolerance threshold of ±100 nm, ±90 nm, ±80 nm, ±70 nm, ±60 nm, ±50 nm, ±40 nm, ±30 nm, ±20 nm, ±10 nm, ±8 nm, ±6 nm, ±5 nm, ±4 nm, ±3 nm, ±2 nm, ±1 nm, and so forth. In some cases, the emitter includes a plurality of laser bundles that are each configured to pulse a particular wavelength of EMR with a tolerance threshold not greater than ±5 nm, ±4 nm, ±3 nm, or ±2 nm.

The variable pulse cycle may include one or more wavebands of EMR that are tuned for multispectral imaging. These wavebands of EMR are selected to elicit a spectral response from a certain tissue or penetrate through a certain tissue (such that substances disposed behind that tissue may be visualized). The multispectral wavebands of EMR include one or more of the following: 400±50 nm, 410±50 nm, 420±50 nm, 430±50 nm, 440±50 nm, 450±50 nm, 460±50 nm, 470±50 nm, 480±50 nm, 490±50 nm, 500±50 nm, 510±50 nm, 520±50 nm, 530±50 nm, 540±50 nm, 550±50 nm, 560±50 nm, 570±50 nm, 580±50 nm, 590±50 nm, 600±50 nm, 610±50 nm, 620±50 nm, 630±50 nm, 640±50 nm, 650±50 nm, 660±50 nm, 670±50 nm, 680±50 nm, 690±50 nm, 700±50 nm, 710±50 nm, 720±50 nm, 730±50 nm, 740±50 nm, 750±50 nm, 760±50 nm, 770±50 nm, 780±50 nm, 790±50 nm, 800±50 nm, 810±50 nm, 820±50 nm, 830±50 nm, 840±50 nm, 850±50 nm, 860±50 nm, 870±50 nm, 880±50 nm, 890±50 nm, 900±50 nm, 910±50 nm, 920±50 nm, 930±50 nm, 940±50 nm, 950±50 nm, 960±50 nm, 970±50 nm, 980±50 nm, 990±50 nm, 1000±50 nm, 900±100 nm, 950±100 nm, or 1000±100 nm. The aforementioned wavebands may be finely tuned such that the emitter pulses the central wavelength with a tolerance threshold of ±100 nm, ±90 nm, ±80 nm, ±70 nm, ±60 nm, ±50 nm, ±40 nm, ±30 nm, ±20 nm, ±10 nm, ±8 nm, ±6 nm, ±5 nm, ±4 nm, ±3 nm, ±2 nm, ±1 nm, and so forth. In some cases, the emitter includes a plurality of laser bundles that are each configured to pulse a particular wavelength of EMR with a tolerance threshold not greater than ±5 nm, ±4 nm, ±3 nm, or ±2 nm.

Certain multispectral wavelengths pierce through tissue and enable a medical practitioner to "see through" tissues in the foreground to identify chemical processes, structures, compounds, biological processes, and so forth that are located behind the foreground tissues. The multispectral wavelengths may be specifically selected to identify a specific disease, tissue condition, biological process, chemical process, type of tissue, and so forth that is known to have a certain spectral response.

The variable pulse cycle may include one or more emissions of EMR that are optimized for mapping imaging, which includes, for example, three-dimensional topographical mapping, depth map generation, calculating distances between objects within a scene, calculating dimensions of objects within a scene, determining whether a tool or other object approaches a threshold distance from another object, and so forth. The pulses for laser mapping imaging include EMR formed in a mapping pattern, which may include one or more of vertical hashing, horizontal hashing, a dot array, and so forth.

The controller 104 optimizes the variable pulse cycle to accommodate various imaging and video standards. In most use-cases, the system outputs a video stream comprising at least 30 frames per second (fps). The controller 104 synchronizes operations of the emitter and the image sensor to output data at a sufficient frame rate for visualizing the scene and further for processing the scene with one or more advanced visualization techniques. A user may request a real-time color video stream of the scene and may further request information based on one or more of multispectral imaging, fluorescence imaging, or laser mapping imaging (which may include topographical mapping, calculating dimensions and distances, and so forth). The controller 104 causes the image sensor to separately sense color data frames, multispectral data frames, fluorescence data frames, and mapping data frames based on the variable pulse cycle of the emitter.

In some cases, a user requests more data types than the system can accommodate while maintaining a smooth video frame rate. The system is constrained by the image sensor's ability to accumulate a sufficient amount of electromagnetic energy during each blanking period to output a data frame with sufficient exposure. In some cases, the image sensor outputs data at a rate of 60-120 fps and may specifically output data at a rate of 60 fps. In these cases, for example, the controller 104 may devote 24-30 fps to color visualization and may devote the other frames per second to one or more advanced visualization techniques.

The controller 104 calculates and adjusts the variable pulse cycle of the emitter 102 in real-time based at least in part on the known capabilities of the pixel array 125. The controller 104 may access data stored in memory indicating how long the pixel array 125 must be exposed to a certain waveband of EMR for the pixel array 125 to accumulate a sufficient amount of EMR to output a data frame with sufficient exposure. In most cases, the pixel array 125 is inherently more or less sensitive to different wavebands of EMR. Thus, the pixel array 125 may require a longer or shorter blanking period duration for some wavebands of EMR to ensure that all data frames output by the image sensor 124 comprise sufficient exposure levels.

Figure 3A:
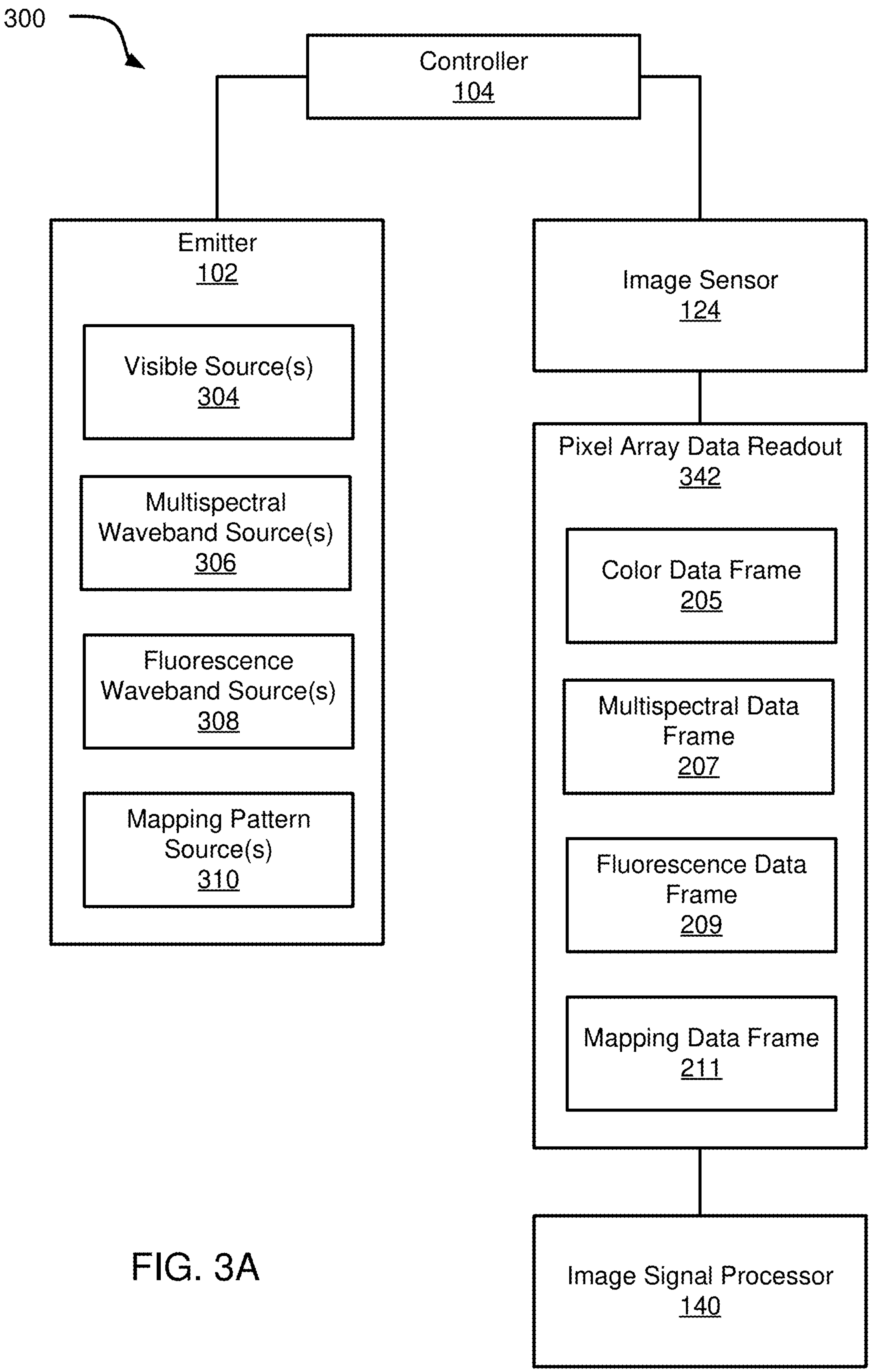
FIG. 3A is a schematic block diagram of an example system for processing data output by an image sensor with a controller in communication with an emitter and the image sensor.
Figure 3B:
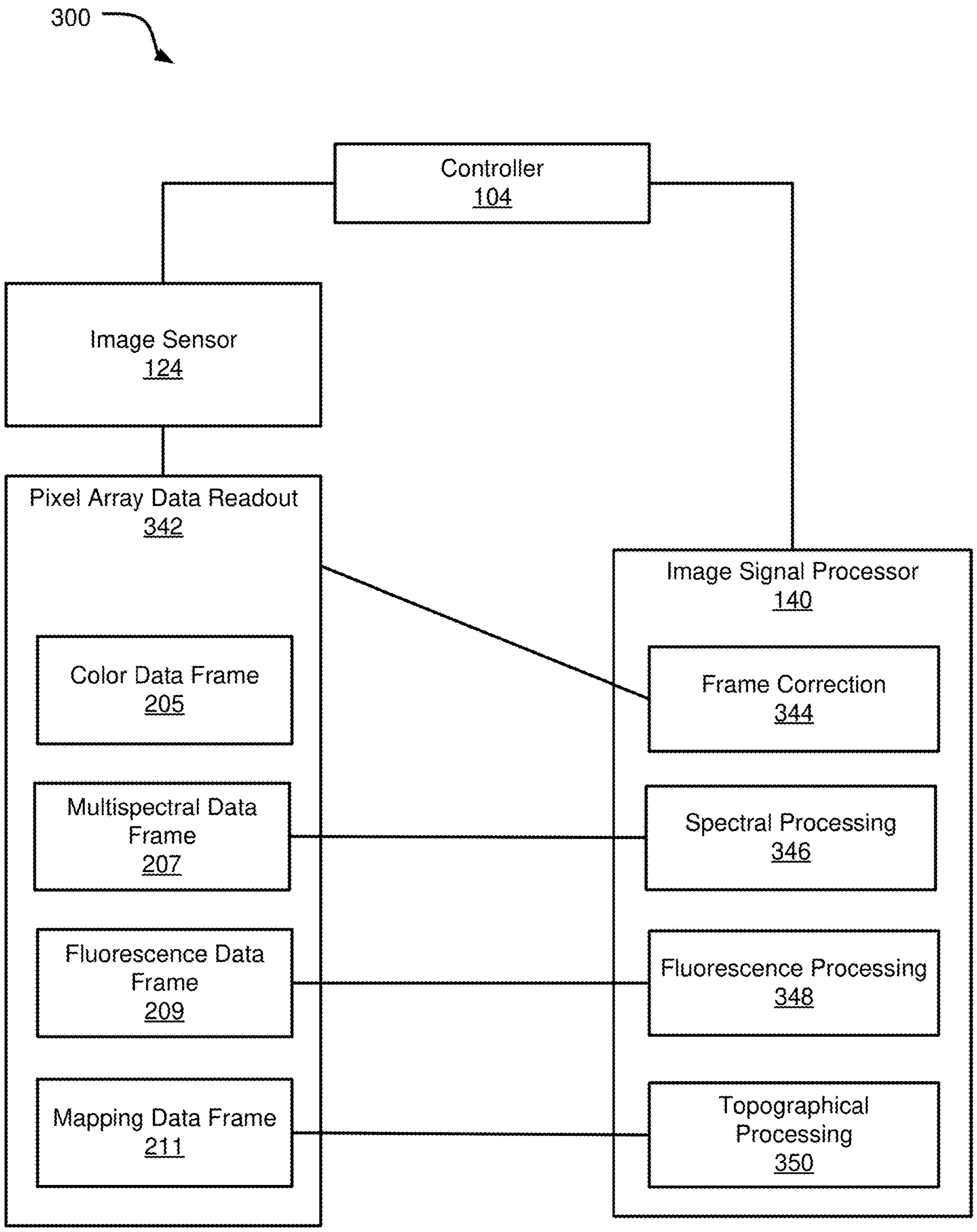
FIG. 3B is a schematic block diagram of an example system for processing data output by an image sensor to generate color imaging data and advanced imaging data.

The controller 104 determines the data input requirements for various advanced visualization algorithms (see, e.g., the algorithms 346, 348, 350 first described in FIG. 3B). For example, the controller 104 may determine that certain advanced visualization algorithms do not require a data input at the same regularity as a color video stream output of 30 fps. In these cases, the controller 104 may optimize the variable pulse cycle to include white light pulses at a more frequent rate than pulses for advanced visualization such as multispectral, fluorescence, or laser mapping imaging. Additionally, the controller 104 determines whether certain algorithms may operate with lower resolution data frames that are read out by the image sensor using a pixel binning configuration. In some cases, the controller 104 ensures that all color frames provided to a user are read out in high-resolution (without pixel binning). However, some advanced visualization algorithms (see e.g., 346, 348, 350) may execute with lower resolution data frames.

The system 100 may include a plurality of image sensors 124 that may have different or identical pixel array configurations. For example, one image sensor 124 may include a monochromatic or "color agnostic" pixel array with no filters, another image sensor 124 may include a pixel array with a Bayer pattern CFA, and another image sensor 124 may include a pixel array with a different CFA. The multiple image sensors 124 may be assigned to detect EMR for a certain imaging modality, such as color imaging, multispectral imaging, fluorescence imaging, or laser mapping imaging. Further, each of the image sensors 124 may be configured to simultaneously accumulate EMR and output a data frame, such that all image sensors are capable of sensing data for all imaging modalities.

The controller 104 prioritizes certain advanced visualization techniques based on the user's ultimate goals. In some cases, the controller 104 prioritizes outputting a smooth and high-definition color video stream to the user above other advanced visualization techniques. In other cases, the controller 104 prioritizes one or more advanced visualization techniques over color visualization, and in these cases, the output color video stream may appear choppy to a human eye because the system outputs fewer than 30 fps of color imaging data.

For example, a user may indicate that a fluorescent reagent has been administered to a patient. If the fluorescent reagent is time sensitive, then the controller 104 may ensure that a sufficient ratio of frames is devoted to fluorescence imaging to ensure the user receives adequate fluorescence imaging data while the reagent remains active. In another example, a user requests a notification whenever the user's tool comes within a threshold distance of a certain tissue, such as a blood vessel, nerve fiber, cancer tissue, and so forth. In this example, the controller 104 may prioritize laser mapping visualization to constantly determine the distance between the user's tool and the surrounding structures and may further prioritize multispectral or fluorescence imaging that enables the system to identify the certain tissue. The controller 104 may further prioritize color visualization to ensure the user continues to view a color video stream of the scene.

Figure 3C:
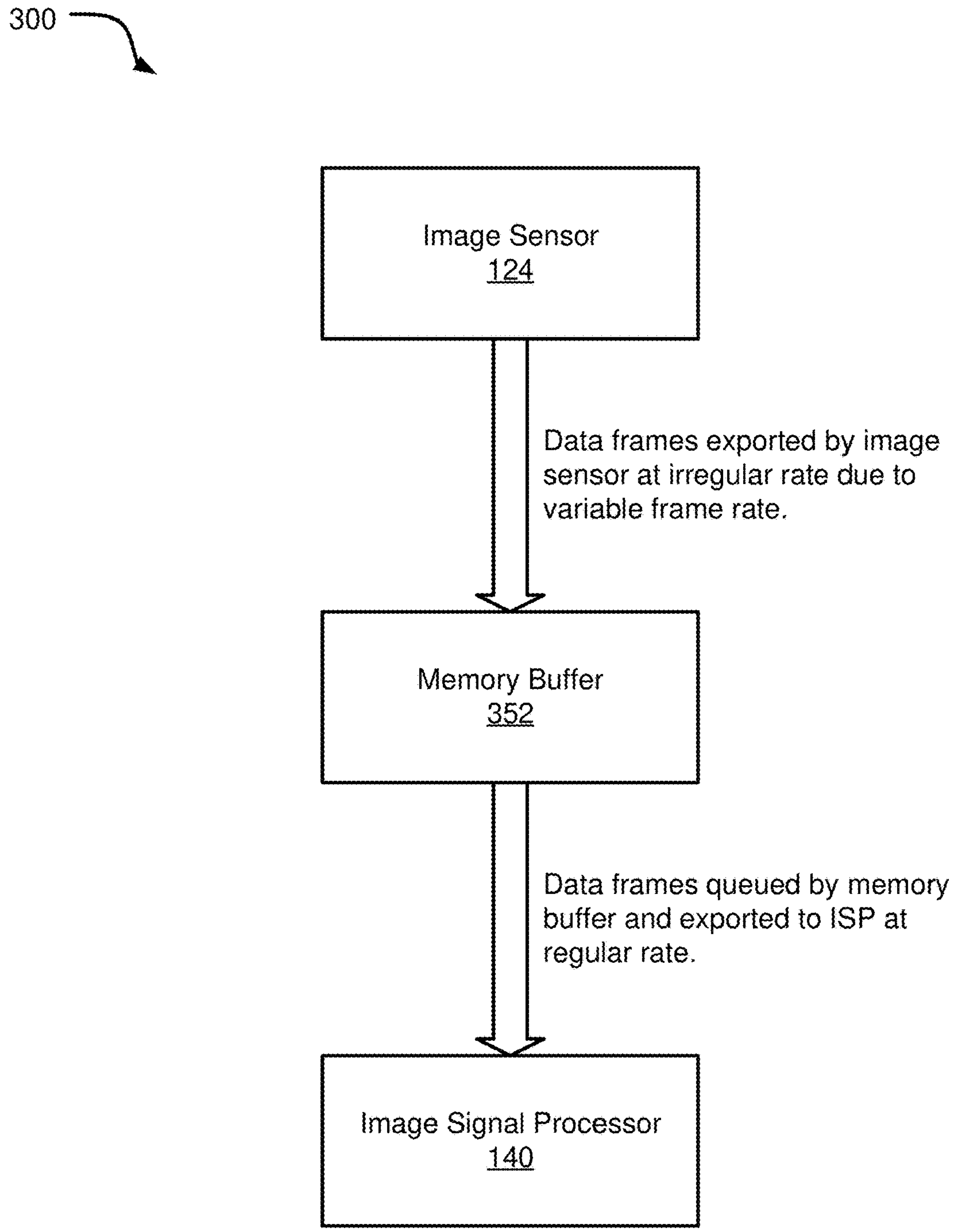
FIG. 3C is a schematic block diagram of an example system for processing data through a memory buffer to provide data frames to an image signal processor at regular intervals.

FIGS. 3A-3C illustrate schematic diagrams of a system 300 for processing data output by an image sensor 124 comprising the pixel array 125. The system 300 includes a controller 104 in communication with each of the emitter 102 and the image sensor 124 comprising the pixel array 125. The emitter 102 includes one or more visible sources 304, multispectral waveband sources 306, fluorescence waveband sources 308, and mapping pattern sources 310 of EMR. The pixel array data readout 342 of the image sensor 124 includes one or more of the color data frames 205, multispectral data frames 207, fluorescence data frames 209, and mapping data frames 211 as discussed in connection with FIG. 2B.

As illustrated in FIG. 3B, all data read out by the pixel array may undergo frame correction 344 processing by the image signal processor 140. In various implementations, one or more of the color data frame 205, the multispectral data frame 207, the fluorescence data frame 209, and the mapping data frame 211 undergoes frame correction 344 processes. The frame correction 344 includes one or more of sensor correction, white balance, color correction, or edge enhancement.

The multispectral data frame 207 may undergo spectral processing 346 that is executed by the image signal processor 140 and/or another processor that is external to the system 300. The spectral processing 346 may include a machine learning algorithm and may be executed by a neural network configured to process the multispectral data frame 207 to identify one or more tissue structures within a scene based on whether those tissue structures emitted a spectral response.

The fluorescence data frame 209 may undergo fluorescence processing 348 that is executed by the image signal processor 140 and/or another processor that is external to the system 300. The fluorescence processing 348 may include a machine learning algorithm and may be executed by a neural network configured to process to fluorescence data frame 209 and identify an intensity map wherein a fluorescence relaxation wavelength is detected by the pixel array.

The mapping data frame 211 may undergo topographical processing 350 that is executed by the image signal processor 140 and/or another processor that is external to the system 300. The topographical processing 350 may include a machine learning algorithm and may be executed by a neural network configured to assess time-of-flight information to calculate a depth map representative of the scene. The topographical processing 350 includes calculating one or more of a three-dimensional topographical map of the scene, a dimension of one or more objects within the scene, a distance between two or more objects within the scene, a distance between a tool and a certain tissue structure within the scene, and so forth.

FIG. 3C illustrates a schematic diagram of a system 300 and process flow for managing data output at an irregular rate. The image sensor 124 operates according to a sensor cycle that includes blanking periods and readout periods. The image sensor 124 outputs a data frame at the conclusion of each readout period that includes an indication of the amount of EMR the pixel array accumulated during the preceding accumulation period or blanking period.

Each frame period in the sensor cycle is adjustable on a frame-by-frame basis to optimize the output of the image sensor and compensate for the pixel array 125 having varying degrees of sensitivity to different wavebands of EMR. The duration of each blanking period may be shortened or lengthened to customize the amount of EMR the pixel array 125 can accumulate. Additionally, the duration of each readout period may be shortened or lengthened by implementing a pixel binning configuration or causing the image sensor to read out each pixel within the pixel array 125. Thus, the image sensor 124 may output data frames at an irregular rate due to the sensor cycle comprising a variable frame rate. The system 300 includes a memory buffer 352 that receives data frames from the image sensor 124. The memory buffer 352 stores the data frames and then outputs each data frame to the image signal processor 140 at a regular rate. This enables the image signal processor 140 to process each data frame in sequence at a regular rate.

Figure 4:
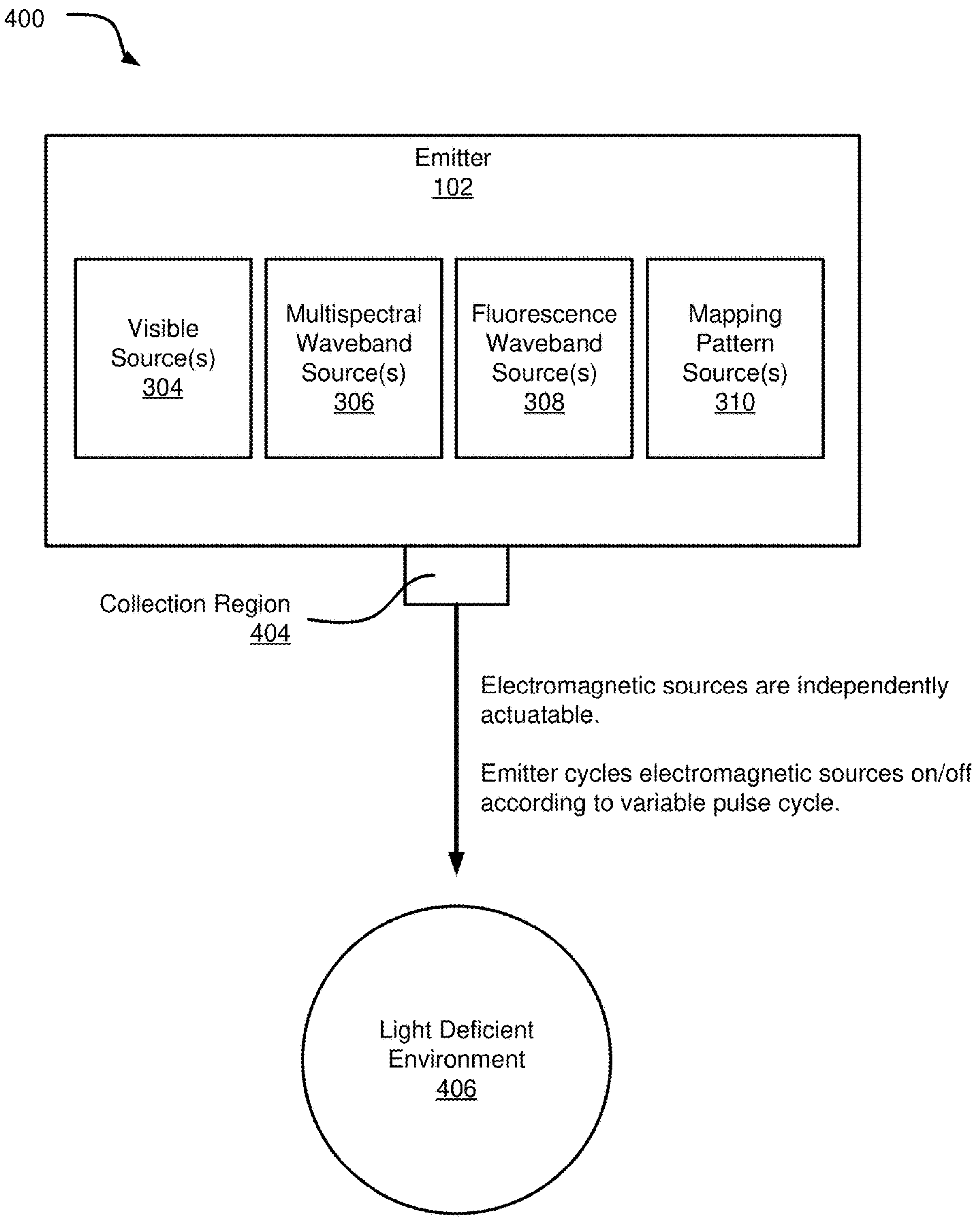
FIG. 4 is a schematic diagram of an illumination system for illuminating a light deficient environment according to a variable pulse cycle.

FIG. 4 is a schematic diagram of an illumination system 400 for illuminating a light deficient environment 406 such as an interior of a body cavity. In most cases, the emitter 102 is the only source of illumination within the light deficient environment 406 such that the pixel array of the image sensor does not detect any ambient light sources. The emitter 102 includes a plurality of separate and independently actuatable sources of EMR, which may include visible source(s) 304, multispectral waveband source(s) 306, fluorescence waveband source(s) 308, and mapping pattern source(s) 310. The emitter may cycle a selection of the sources on and off to pulse according to the variable pulse cycle received from the controller 104. Each of the EMR sources feeds into a collection region 404 of the emitter 102. The collection region 404 may then feed into a waveguide (see e.g., 130 in FIG. 1A) that transmits the pulsed EMR to a distal end of an endoscope within the light deficient environment 406.

The variable pulsing cycle is customizable and adjustable in real-time based on user input. The emitter 102 may instruct the individual EMR sources to pulse in any order. Additionally, the emitter 102 may adjust one or more of a duration or an intensity of each pulse of EMR. The variable pulse cycle may be optimized to sufficiently illuminate the light deficient environment 406 such that the resultant data frames read out by the pixel array 125 are within a desired exposure range (i.e., the frames are neither underexposed nor overexposed). The desired exposure range may be determined based on user input, requirements of the image signal processor 140, and/or requirements of a certain image processing algorithm (see 344, 346, 348, and 350 in FIG. 3B). The sufficient illumination of the light deficient environment 406 is dependent on the energy output of the individual EMR sources and is further dependent on the efficiency of the pixel array 125 for sensing different wavebands of EMR.

Figure 5:
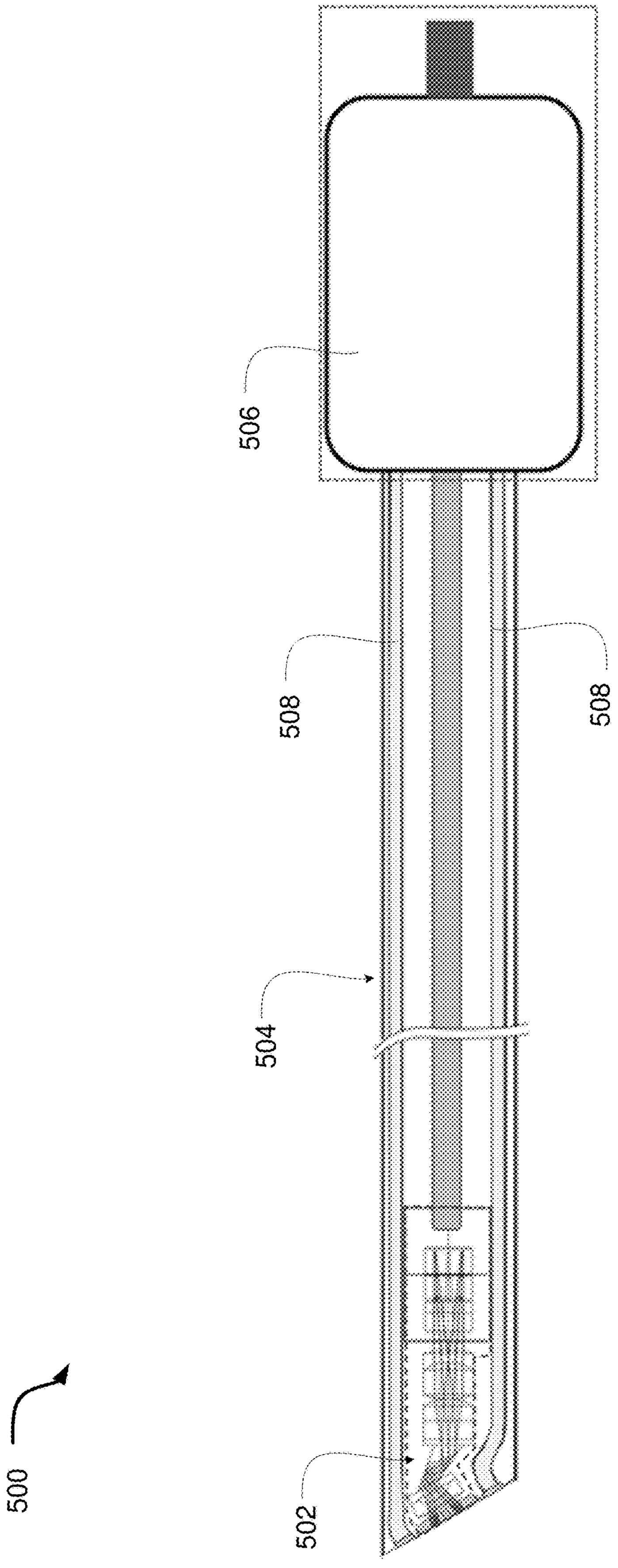
FIG. 5 is a schematic illustration of a cross-sectional side view of an endoscopic comprising dual image sensors disposed within an interior space defined by the endoscope tube.

FIG. 5 is a schematic illustration of a cross-sectional side view of a system 500 for endoscopic visualization with two or more image sensors. The system 500 is capable of outputting three-dimensional (stereo) visualization data. The system 500 includes an endoscope tube 504 with a lens assembly 502 disposed with an interior cavity defined by the endoscope tube 504. The system 500 provides illumination to a scene by way of one or more waveguides 508 comprising a fiber optic bundle that transmits light from the emitter 102 (not shown in FIG. 5) to a distal end of the endoscope tube 504. The system 500 includes a handpiece unit 506 that may be equipped with a microcontroller 122, electronic cables, and other components. The system 500 provides a distal tip window surface having a 30° direction of view adjustment with respect to a longitudinal axis defined by the endoscope tube 504.

Endoscopy is a powerful means of providing minimally invasive surgery procedures such as appendectomy, hysterectomy, nephrectomy, and so forth. Typically, the challenge with endoscopic systems (and laparoscopic systems and particular) include minimizing the image acquisition head size, optimizing a tradeoff between field of view (FOV) and spatial resolution, and enabling the endoscope to be utilized to acquire a wide range of working distances. For many applications, it is desirable to dispose all image acquisition components within an endoscope tube having a diameter of 8.7 mm or less. The lens assembly 502 is designed to be disposed within such a highly space constrained environment.

Figure 6A:
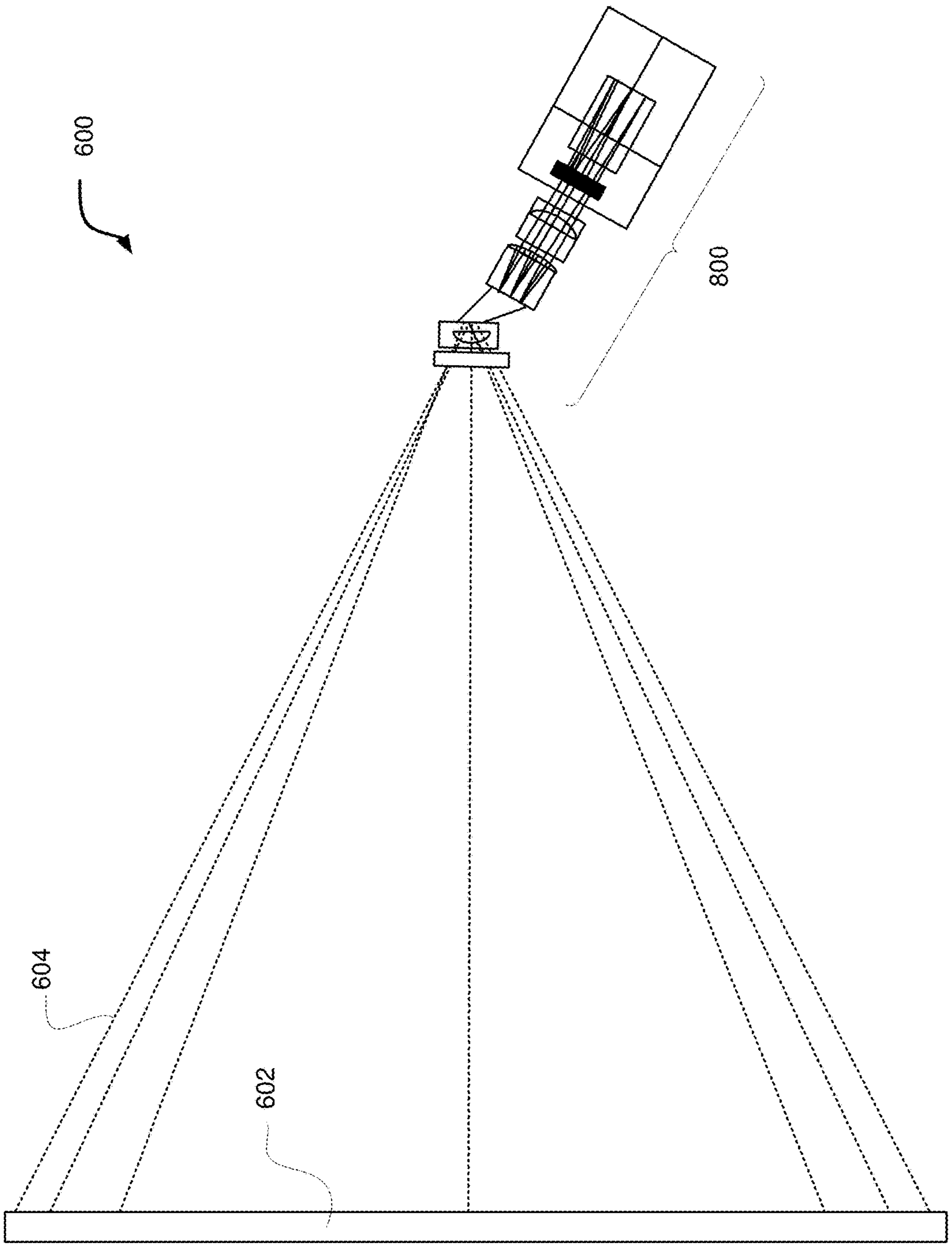
FIG. 6A is a schematic illustration of a cross-sectional side view of a system comprising a lens assembly for propagating an image beam from an object to an image sensor, wherein the lens assembly provides a 30° direction of view adjustment relative to the endoscope tube.
Figure 6B:
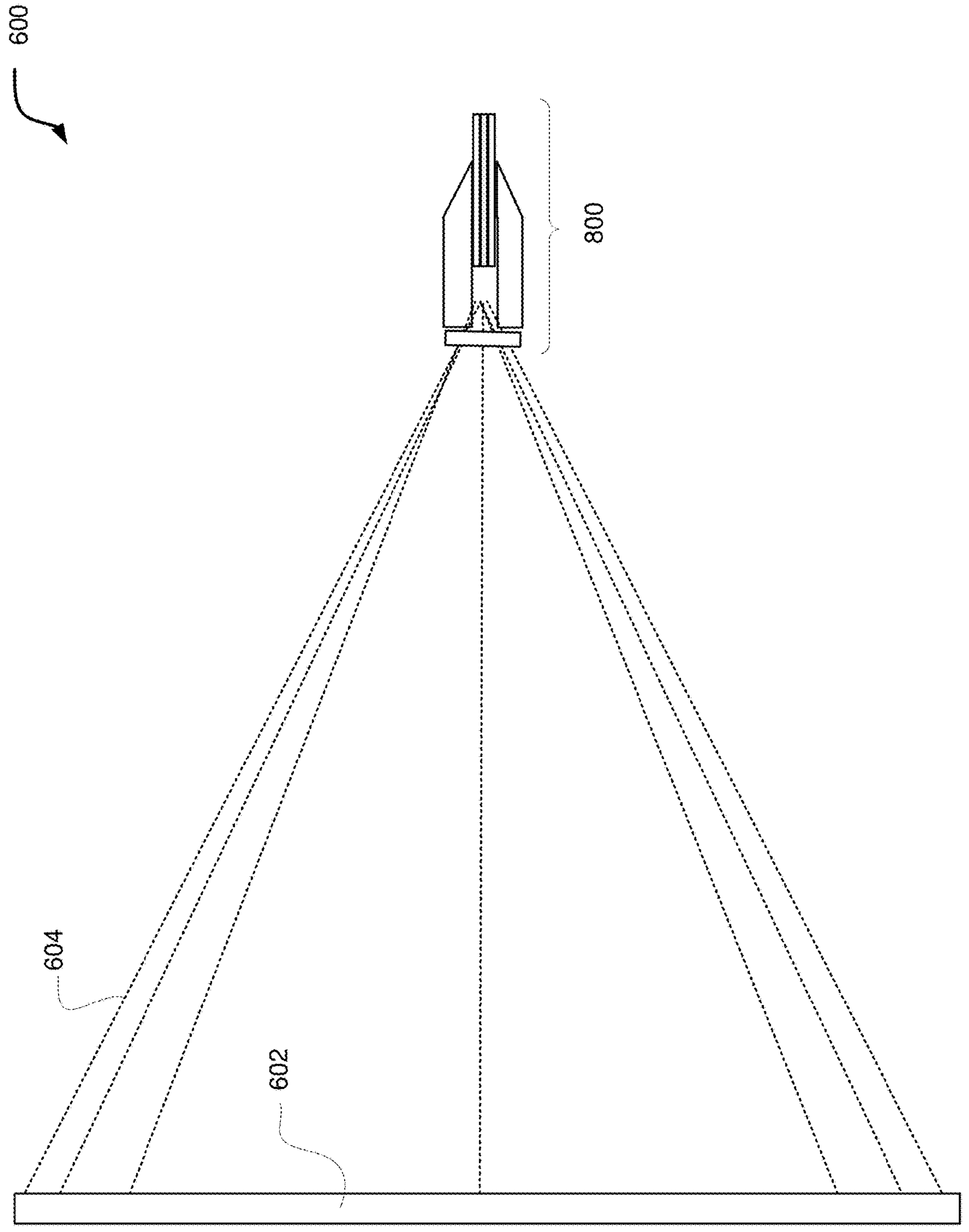
FIG. 6B is a schematic illustration of a cross-sectional top-down aerial view of a system comprising a lens assembly for propagating an image beam from an object to an image sensor, wherein the lens assembly provides a 30° direction of view adjustment relative to the endoscope tube.

FIGS. 6A and 6B are schematic illustrations of a system 600 comprising a lens assembly 800 for propagating an image beam from an object to a window. The system 600 includes the lens assembly 800 discussed in connection with FIGS. 8A-8B. The system 600 provides a thirty-degree (30°) direction of view adjustment with respect to a longitudinal axis defined by the endoscope tube. FIG. 6A is a cross-sectional side view of the system 600 and FIG. 6B is a top-down aerial view of the system 600.

Figure 7A:
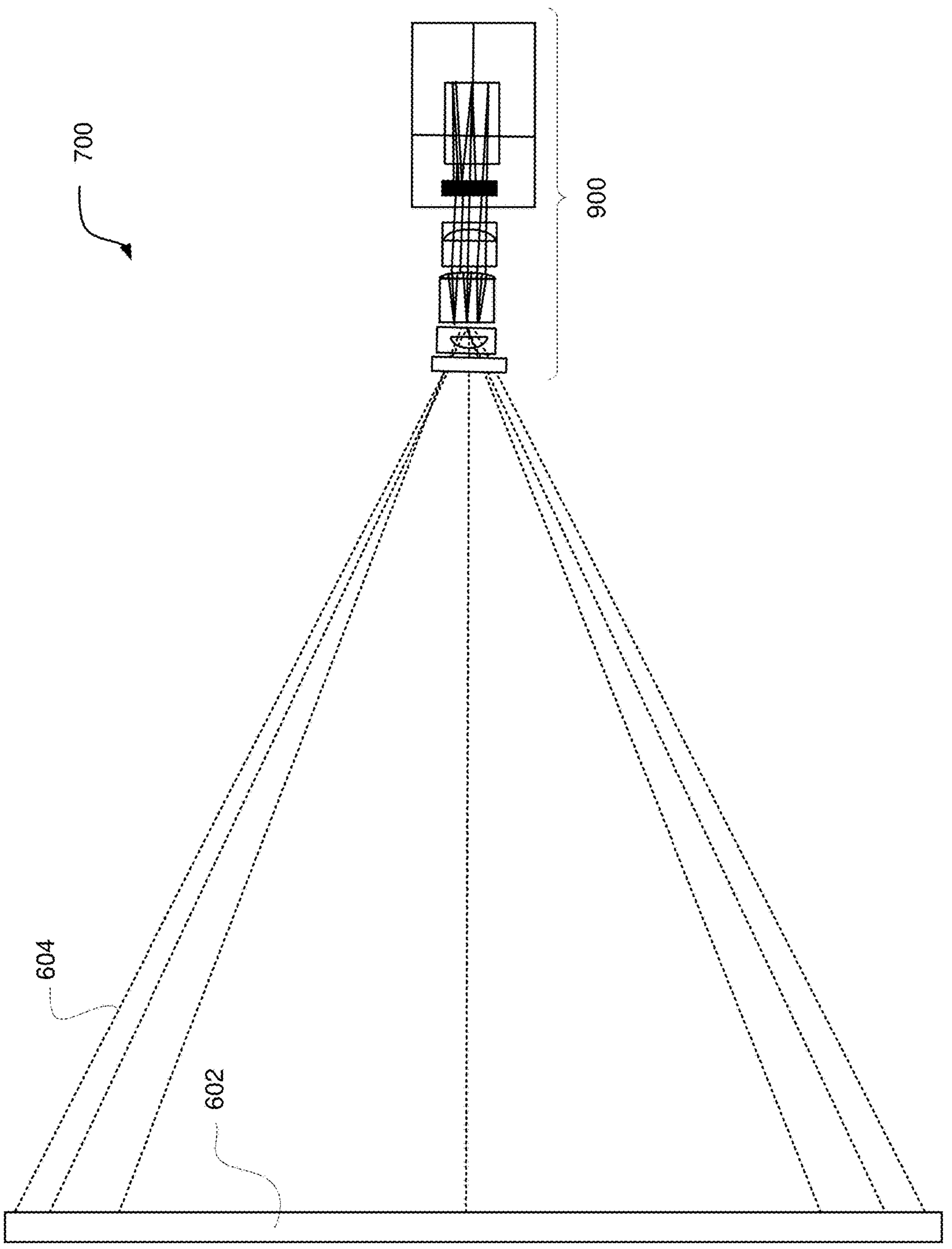
FIG. 7A is a schematic illustration of a cross-sectional side view of a system comprising a lens assembly for propagating an image beam from an object to an image sensor, wherein the lens assembly provides a 0° direction of view adjustment relative to the endoscope tube.
Figure 7B:
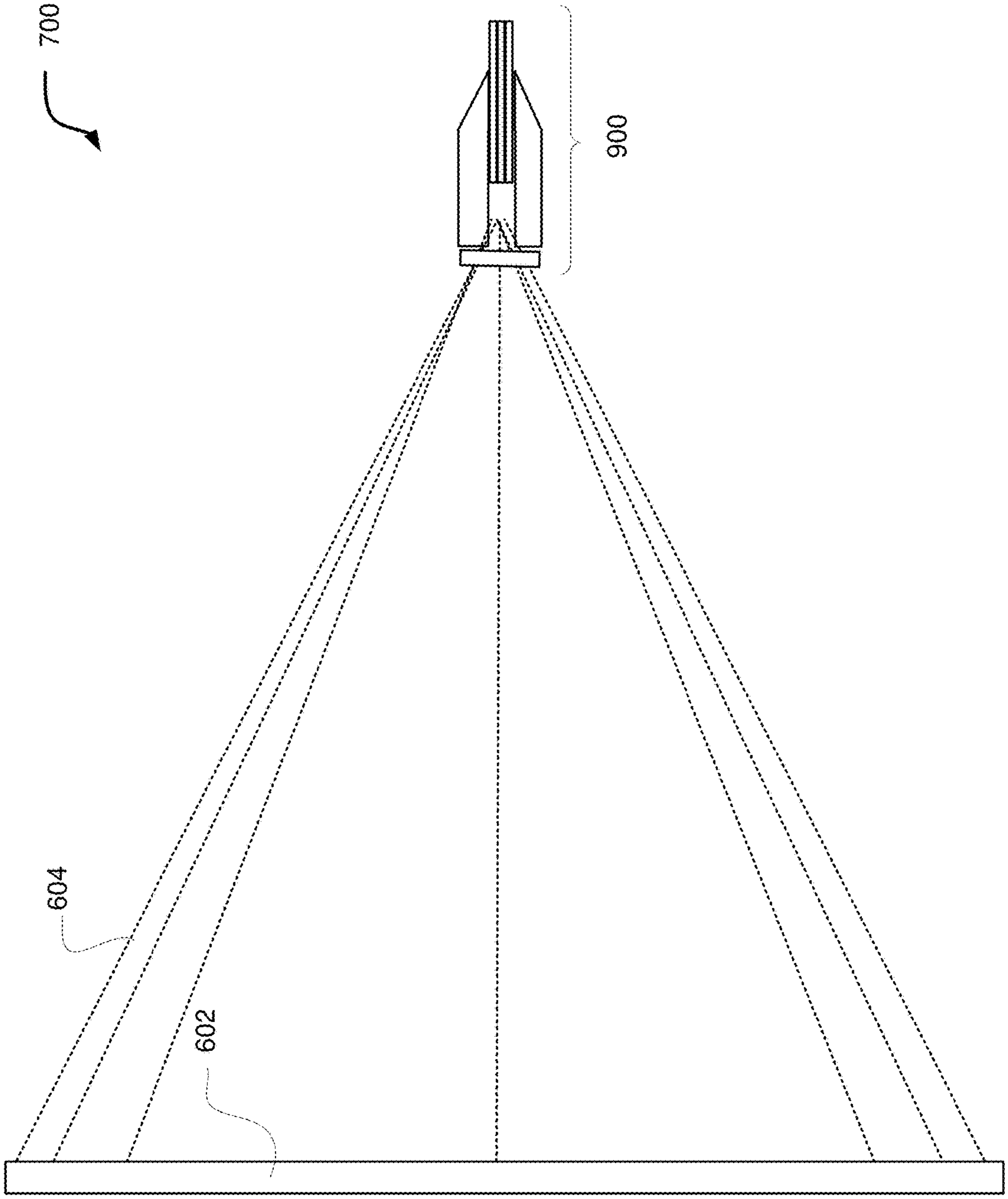
FIG. 7B is a schematic illustration of a cross-sectional top-down aerial view of a system comprising a lens assembly for propagating an image beam from an object to an image sensor, wherein the lens assembly provides a 0° direction of view adjustment relative to the endoscope tube.

FIGS. 7A and 7B are schematic illustrations of a system 700 comprising a lens assembly 900 for propagating an image beam from an object 602 to a window of the lens assembly 900. The system 700 includes the lens assembly 900 discussed in connection with FIGS. 9A-9B. The system 700 provides a zero-degree (0°) direction of view adjustment with respect to a longitudinal axis defined by the endoscope tube. FIG. 7A is a cross-sectional side view of the system 700 and FIG. 7B is a top-down aerial view of the system 700.

FIGS. 6A-6B and 7A-7B illustrate how a scattered or reflected beam of EMR (i.e., the image beam 604) propagates from an object 602 to a window of the lens assembly 800. The image beam 604 then propagates through the lens assembly 800 to irradiate the pixel arrays 125 of two or more image sensors 124. Specifically, the image beam 604 propagates through one or more of a negative lens, a prism, a positive lens group, and folding beam prism, before irradiating the image sensor 124. The exact configuration of the lens assembly 800, 900 may be adjusted and optimized as described further herein. The systems 600, 700 enable the image sensor 124 to be irradiated with visible EMR (may specifically include white light), fluorescence excitation EMR, and/or multispectral EMR as discussed herein. The image sensor 124 converts an accumulated optical signal to an electronic video signal, which is then transmitted to the microcontroller 122 and/or controller 104.

The systems 600, 700 can be used to acquire visible light images (may specifically include white light or color images), near infrared fluorescence images, narrowband visible multispectral images, narrowband near infrared multispectral images, and other image types as described herein. For example, in a visible image acquisition mode, a waveguide 130, 131 transmits visible EMR from the emitter 102 to a distal end of the endoscope tube 504. The visible EMR then illuminates the object 602. A portion of the scattered visible EMR from the object 602 is collected by the imaging system, which converts the optical signal to an electronic video signal.

Further for example, in a near infrared fluorescence mode, the waveguide 130, 131 transmits near infrared fluorescence excitation EMR from the emitter 102 to a distal end of the endoscope tube 504, wherein the near infrared EMR illuminates the object 602. A fluorescence fluorophore or auto fluorescing tissue on the object 602 surface absorb the near infrared EMR and emit a near infrared fluorescence relaxation emission. A portion of the near infrared fluorescence relaxation emission is collected by the imaging system. The imaging system converts the optical signal to an electronic video signal.

Figure 8A:
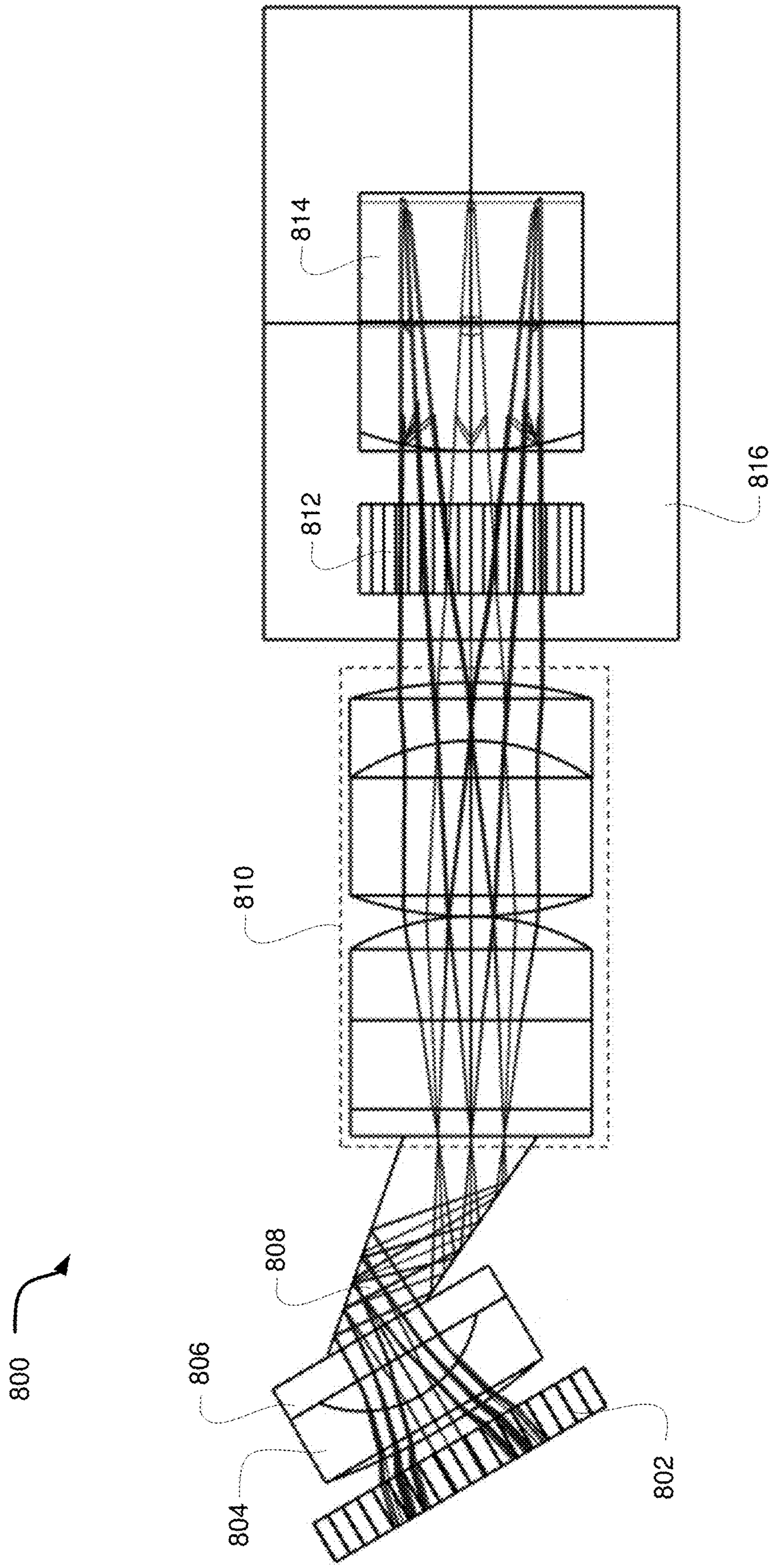
FIG. 8A is a schematic illustration of a cross-sectional side view of a lens assembly providing a 30° direction of view adjustment.
Figure 8B:
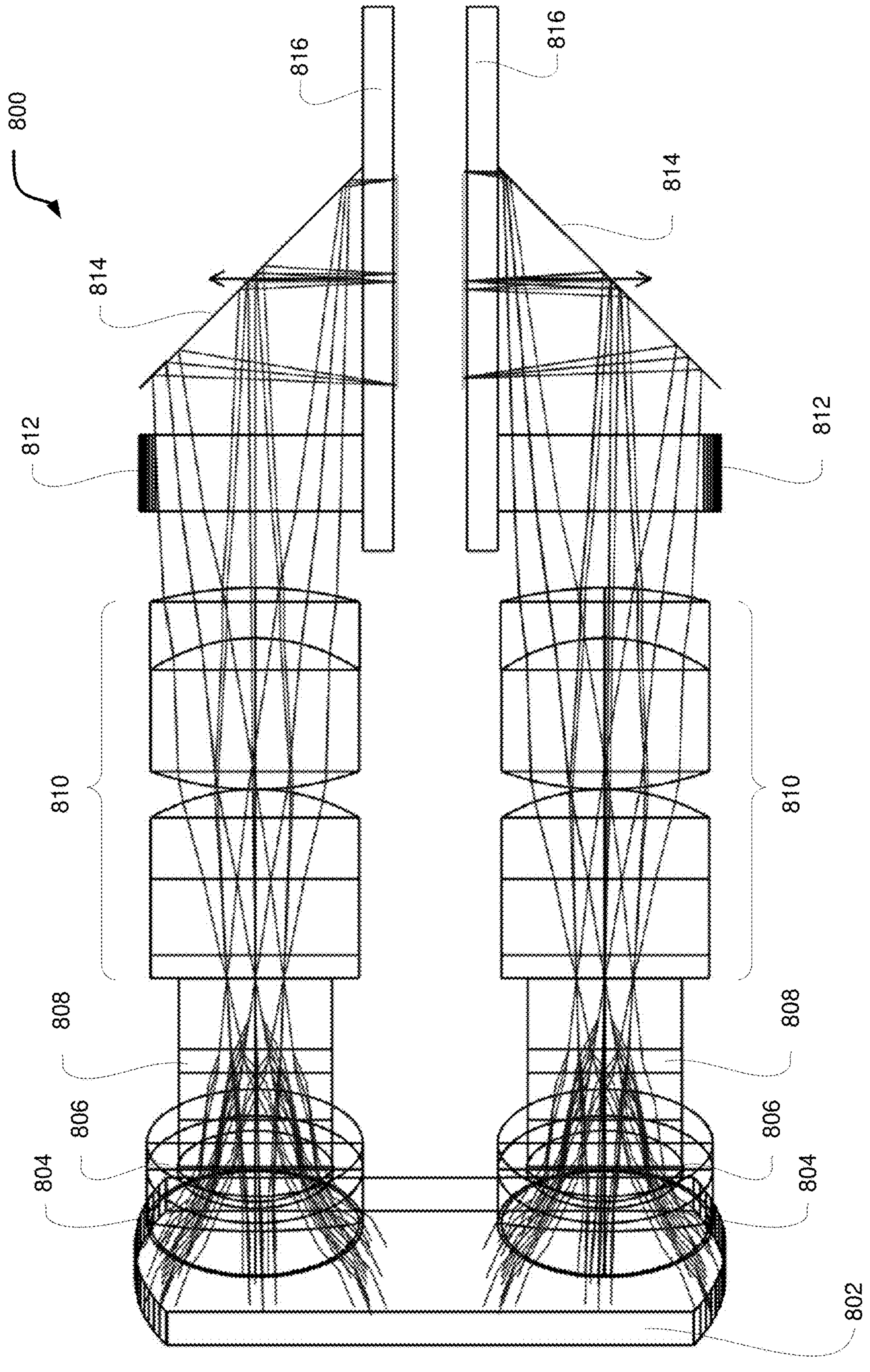
FIG. 8B is a schematic illustration of a cross-sectional top-down aerial view of a lens assembly providing a 30° direction of view adjustment.

FIGS. 8A and 8B are schematic illustrations of a lens assembly 800 for providing a 30° direction of view. The optical visualization system 106 of the system 100 may include all components of the lens assembly 800 for receiving beams of EMR and directing the EMR to the image sensors 124. The lens assembly 800 may be implemented in the system 600 illustrated in FIGS. 6A-6B. The lens assembly 800 includes a window 802, negative lens 804, aperture stop plate 806, direction-of-view (DOV) prism 808 (in the example illustrated in FIGS. 8A-8B, the DOV prism 808 is a 30° prism), positive lens group 810, filter 812, 900 beam folding prism 814, and image sensor printed circuit board (PCB) 816.

The window 802 is a transparent wall that allows EMR to pass through. The window 802 serves as a transparent protective cover that protects the internal components of the lens assembly 800. In some cases, the window 802 is constructed of an ultrahard transparent material such as sapphire crystal, chemically strengthened glass, tempered glass, laminated glass, or other hard material.

The negative lens 804 has a negative focal length and may alternatively be referred to as a diverging lens or concave lens. The negative lens 804 is specifically a negative meniscus lens wherein the lens is convex on the object side and concave on the image sensor 124 side. As shown in FIG. 8A, the negative lens 804 is characterized by its thinner center and thicker edges.

If rays of EMR were passing from right to left across FIGS. 8A-8B, the negative lens 804 would cause those rays of EMR to diverge (spread out). When parallel rays of EMR pass through the negative lens 804, the rays refract (bend) away from the axis of the negative lens 804, and this causes the rays to diverge. When reflected EMR scatters off a scene and passes through the lens assembly (i.e., from left to right across FIGS. 8A-8B), the negative lens 804 performs the opposite function, and causes those rays to converge on the aperture stop plate 806. The light bending characteristics of the negative lens 804 depend on the shape, curvature, and refractive index of the negative lens 804, which are optimized to cause EMR to converge on to the aperture stop plate 806.

The aperture stop plate 806 controls the amount of EMR that enters the lens assembly 800 and is permitted to irradiate the pixel array 125 of the image sensor 124. The aperture stop plate 806 comprises a plate or disk with a precisely defined aperture or opening through which EMR may pass. The main purpose of the aperture stop plate 806 is to limit the size of a beam of EMR entering the lens assembly 800 and irradiating the image sensor 124. This in turn impacts the depth of field, resolution, and overall image quality of the resultant data frames 205, 207, 209, 211.

The aperture stop plate 806 serves as a physical barrier that restricts the size of the beam of EMR passing through it. By adjusting the size of the aperture, the amount of EMR reaching the image sensor 124 may be controller. This helps to regulate the exposure and depth of field in the resultant data frames 205, 207, 209, 211. The size of the aperture is determined by the diameter of the opening in the aperture stop plate 806. Aperture sizes are often specified as f-numbers, which represent the ratio of the focal length of the lens to the diameter of the aperture. Common aperture settings include f/2.8, f/4, f/5.6, and so on. Smaller aperture sizes (i.e., larger f-numbers) result in reduced light transmission but increased depth of field, while larger aperture sizes (i.e., smaller f-numbers) allow addition light to pass through but decrease the depth of field. The aperture stop plate 806 plays an important role in determining the depth of field of the data frames 205, 207, 209, 211 output by the system 100.

The aperture stop plate 806 may additionally impact the optical performance of a lens assembly 800 by influencing the effects of lens aberrations. By adjusting the aperture size, certain types of aberration may be minimized or controller for improved image quality.

The aperture stop plate 806 may have various geometries, such as circular, elliptical, rectangular, or custom shapes. The choice of shape depends on the specific requirements of the implementation and the desired characteristics of the resultant images.

The lens assembly 800 may additionally include a match plate, which may include components of the aperture stop plate 806 or may be a separate component. A match plate is used to ensure accurate alignment and assembly of components of the lens assembly 800. The aperture match plate may be designed with features or guides that match corresponding features on neighboring components, including the negative lens 804 and the DOV prism 808. These guides allow for precise positioning and alignment during the assembly process and ensure consistency and accuracy in the final lens assembly 800.

The direction-of-view (DOV) prism 808 depicted in FIGS. 8A-8B is an optical prism with an angle of 30 degrees. In other embodiments, the DOV prism 808 is configured with another angle such as 0°, 5°, 10°, 15°, 20°, 25°, 35°, 40°, 45°, 50°, 55°, 60°, 65°, 70°, 75°, 80°, 85°, and so forth. The DOV prism 808 is a transparent optical element with flat polished surfaces that refract (bend) EMR, and thus cause the rays of EMR to change direction. The DOV prism 808 is typically manufactured of glass but may be manufactured of other materials.

The DOV prism 808 is characterized by its geometry, which comprises two triangular faces meeting at a 30-degree angle. Incoming rays of EMR enter one face of the DOV prism 808 (at the side adjacent to the aperture stop plate 806), undergo internal reflection or refraction, and then exit through the other face of the DOV prism 808 (at the side adjacent to the positive lens group 810). The specific path of the EMR rays depends on the refractive index of the prism material and the angle of incidence.

The positive lens group 810 is a configuration and arrangement of multiple positive lenses (i.e., converging lenses). The positive lens group 810 specifically includes a positive lens and a doublet lens. The positive lenses within the positive lens group 810 have a convex shape, where the center is thicker than the edges. The positive lens group 810 is optimized to manipulate EMR rays and achieve specific optical functions. By combining multiple positive lenses, the optical lens group 810 effectively distributes EMR rays on to the filter 812 and ultimately on to the pixel arrays 125 of the image sensors 124. The positive lens group 810 functions to create a clean and well-defined image output by the image sensors 124.

The specific configuration and arrangement of the positive lenses in the positive lens group 810 can vary depending on the desired optical characteristics and requirements of the system. The combination and alignment of multiple lenses within the positive lens group 810 allows for control of focal length, field of view, aberration correction, and other optical properties.

The filter 812 may specifically include a notch filter 812, which may alternatively be referred to as a band-stop filter or reject filter. The filter 812 is specifically configured to block certain wavelengths of EMR from reaching the image sensor 124. In the embodiments described herein, the filter 812 is typically configured to prevent an excitation wavelength of EMR (see pulsed fluorescence 208) from reflecting off a scene and irradiating the pixel array 125 of the image sensor 124. This thereby ensures the pixel array 125 is only irradiated with a fluorescence relaxation wavelength (emitted by a reagent or tissue) rather than the excitation wavelength emitted by the emitter 102.

The filter 812 is an optical device designed to attenuate or suppress a specific range of frequencies while allowing other frequencies to pass through relatively unaffected. The filter 812 may be implemented using different techniques and technologies and may specifically include any of an electronic notch filter, digital notch filter, or optical notch filter. In most cases, the filter 812 is an optical notch filter, and is designed using specialized coatings or interference techniques that allow light at most wavelengths to pass through while reflecting or absorbing EMR at a particular wavelength or narrowband of wavelengths.

In specific implementations, a lens assembly 800 for stereo visualization may have a different filter 812 in front of each image sensor 124. Specifically, one image sensor 124 may be located “behind” a filter 812 that permits visible EMR to irradiate the pixel array 125 but prevents all near infrared EMR from irradiating the pixel array 125. This type of filter 812 would block both the fluorescence excitation EMR and the fluorescence relaxation EMR from irradiating the pixel array 125. In the same system, a second image sensor 124 may be located behind a filter 812 that blocks the fluorescence excitation EMR from irradiating the pixel array 125 but permits the relaxation wavelength of EMR to irradiate the image sensor. In this system, the second image sensor is configured to output the fluorescence data frames 209.

The beam folding prism 814 may specifically include a 900 beam folding prism but may be equipped with different angles depending on the implementation. The beam folding prism 814 may alternatively be referred to as a reflecting prism or roof prism, and it serves as an optical prism designed to fold or redirect the path of a ray of EMR. The beam folding prism 814 may specifically be configured to change the direction of a ray of EMR by 90 degrees without inverting or reversing the image.

The beam folding prism 814 may specifically be implemented as a roof prism, which comprises two triangular prisms attached together at their bases and forming a right-angle structure. The hypotenuse of each triangular prism serves as the reflecting surface. The incoming rays of EMR enter one face of the beam folding prism 814, reflect off the hypotenuse, and then exit through the adjacent face of the beam folding prism 814.

The beam folding prism 814 allows for compact optical designs by folding the rays of EMR within a confined space. This is particularly useful when the lens assembly 800 is implemented in a highly space constrained environment, such as a small laparoscopic tube. The beam folding prism 814 is designed to minimize light loss and maintain good image quality. However, in some cases, the beam folding prism 814 introduces certain optical effects like phase shifts or polarization changes, and these may be digitally accounted for by an image signal processor of the system 100 or by on-board processing for the image sensor 124 itself.

The image sensor PCB 816 is a specialized circuit board for interfacing with and controlling the image sensor 124. The image sensor PCB 816 provides the necessary electrical connections and signal processing circuitry to capture, process, and transfer data frames 205, 207, 209, 211 from the image sensor to other components of the system 100, such as the microcontroller 122 and controller 104.

The image sensor PCB 816 acts as an interface between the image sensor 124 and other components within the endoscopic visualization system 100. The PCB 816 includes connectors or solder pads to establish electrical connections with the image sensor, and thereby allow for the transfer of power and data signals. The image sensor PCB 816 may additionally provide power supply connections and circuitry to ensure the image sensor 124 receives the required voltage levels and stability. This may include voltage regulation, decoupling capacitors, and other power conditioning components.

In most cases, the image sensor PCB 816 additionally includes signal processing circuitry to enhance image quality and perform various image processing tasks. These tasks may be performed directly by the image sensor PCB 816 or pushed to the microcontroller 122 or controller 104. The PCB 816 may specifically be responsible for performing analog-to-digital conversion, amplifying image data, performing noise reduction, performing edge enhancement, and other signal conditioning components.

The image sensor PCB 816 facilitates the transfer of data frames 205, 207, 209, 211 from the image sensor to other components of the system 100. This may include supporting data communication protocols such as Serial Peripheral Interface (SPI), Inter-Integrated Circuit (I2C), or other custom interfaces. The image sensor PCB 816 is designed to seamlessly integrate with the overall system 100. The PCB 816 may thereby be equipped with additional circuitry and components specific to the particular system 100, such as lens control, image stabilization, or autofocus mechanism.

Figure 9A:
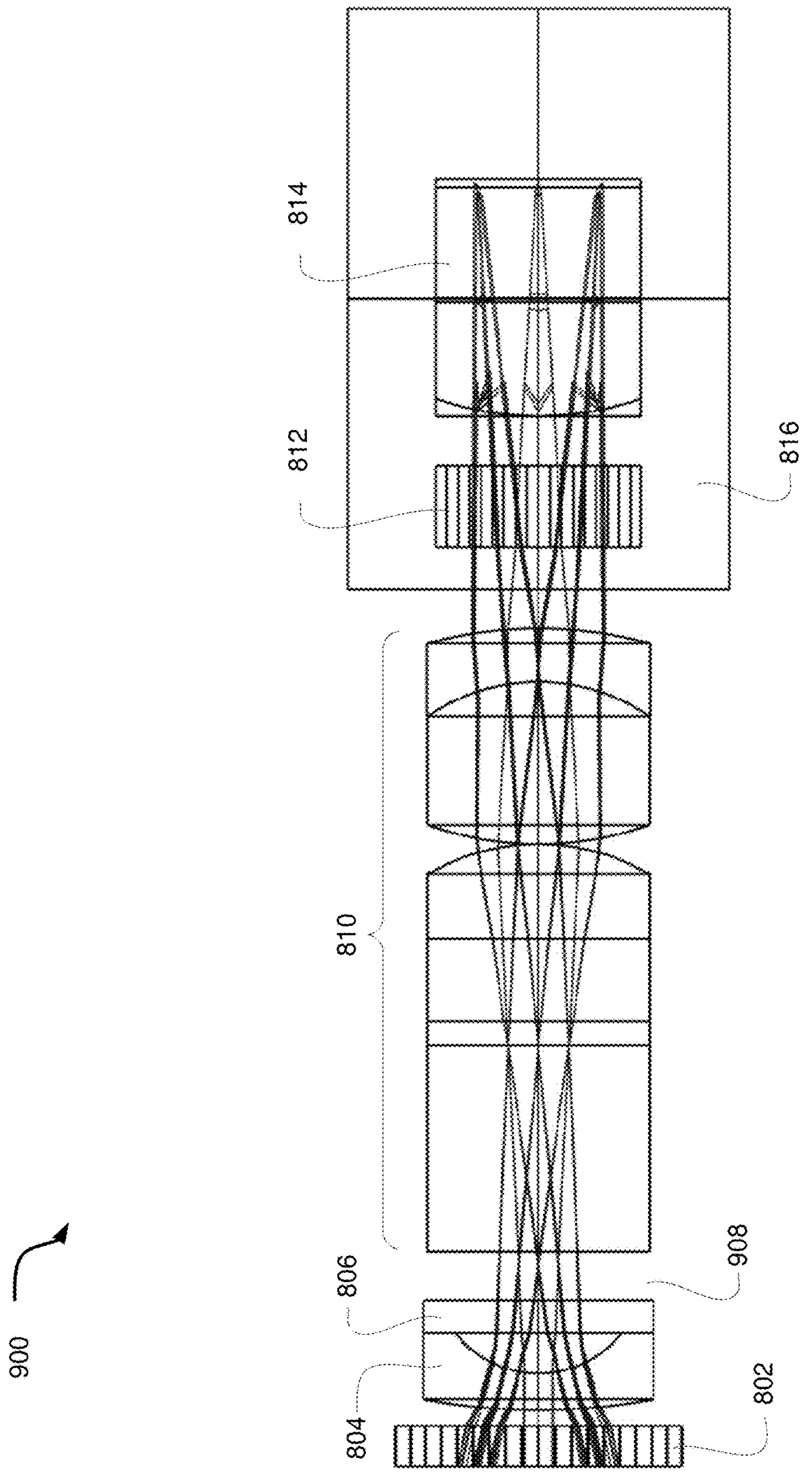
FIG. 9A is a schematic illustration of a cross-sectional side view of a lens assembly providing a 0° direction of view adjustment.
Figure 9B:
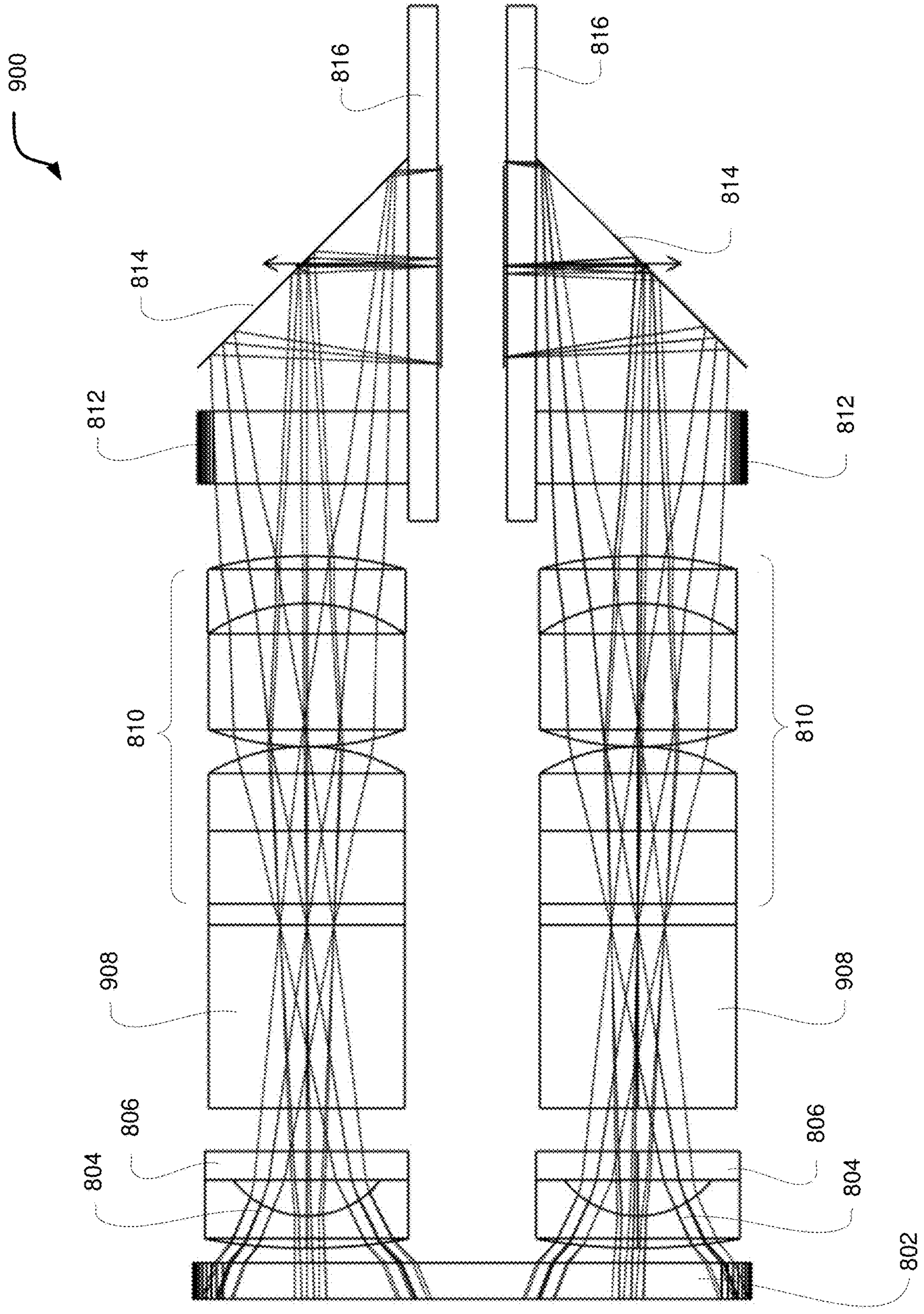
FIG. 9B is a schematic illustration of a cross-sectional top-down aerial view of a lens assembly providing a 0° direction of view adjustment.

FIGS. 9A and 9B are schematic illustrations of a lens assembly 900 for providing a 0° direction of view. The optical visualization system 106 of the system 100 may include all components of the lens assembly 900 for receiving beams of EMR and directing the EMR to the image sensors 124. The lens assembly 900 may be implemented in the system 700 illustrated in FIGS. 7A-7B. Like the lens assembly 800 described in connection with FIGS. 8A-8B, the lens assembly 900 includes the window 802, negative lens 804, aperture stop plate 806, positive lens group 810, filter 812, beam folding prism 814, and image sensor PCB 816. The lens assembly 900 differs from the lens assembly 800 because the lens assembly 900 is implemented with a 0° DOV prism 908 rather than the 30° DOV prism 808 shown in FIGS. 8A-8B. The 0° DOV prism 908 may include a glass rod that provides a zero-degree direction of view adjustment relative to the tube of the endoscope.

In most cases, the system 100 is configured to accept interchangeable laparoscopes tubes that may be equipped with varying directions of view. The direction of view is measured relative to the tube of the laparoscope, such that a 0° direction of view provides zero angular adjustment relative to the tube of the laparoscope. By contrast, a 30° direction of view bends the direction of view 300 relative to the tube of the laparoscope. In FIGS. 8A-8B, the DOV prism 808 changes the primary chief rays of EMR by an angle of 30 degrees relative to the scope tube. In FIGS. 9A-9B, the DOV prism 908 provides no angular adjustment to the primary chief rays o EMR relative to the scope tube. When the direction of view is zero degrees, the DOV prism 908 may consist of a glass rod, as shown in FIGS. 9A-9B.

Figure 10:
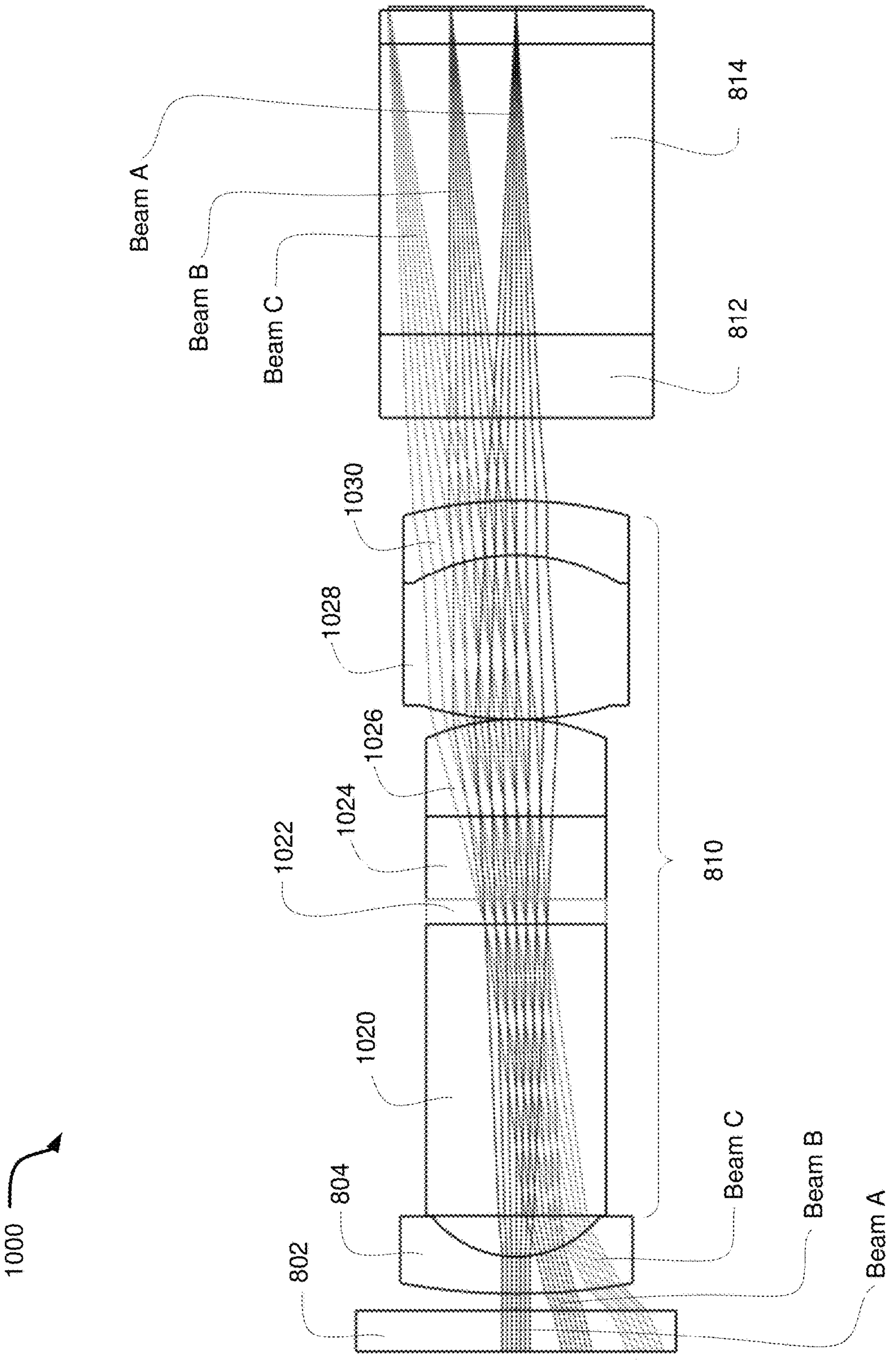
FIG. 10 is a schematic illustration of a cross-sectional side view of a lens assembly.

FIG. 10 is a schematic illustration of a cross-sectional side view a lens assembly 1000. The optical visualization system 106 of the system 100 may include all components of the lens assembly 1000 for receiving beams of EMR and directing the EMR to the image sensors 124. The lens assembly 1000 may be implemented in either of the lens assemblies 800, 900 discussed in connection with FIGS. 8A-8B and FIGS. 9A-9B. The lens assembly 1000 includes the window 802, negative lens 804, positive lens group 810, filter 812, and beam folding prism 814 discussed in connection with FIGS. 8A-8B. The positive lens group 810 comprises a DOV prism 1020, aperture stop 1022, chromatic compensating plate 1024, first convex lens 1026, second convex lens 1028, and concave lens 1030. The DOV prism 1020 provides field compression such that an angle between the lens axis and beam is reduced when entering the DOV prism 1020. In a zero-degree direction of view scope, the DOV prism 1020 may include a glass rod. In a 30-degree direction of view scope, the DOV prism 1020 may look like the DOV prism 808 shown in more detail in FIG. 11. The aperture stop 1022 is configured to block rays outside a designated field of view, and further to block EMR scattered within the lens assembly. The chromatic compensating plate 1030 reduces the lens group focal length difference for different colors or wavebands of EMR.

The second convex lens 1028 and the concave lens 1030 form a doublet lens. Thus, the doublet lens of the positive lens group 810 comprises the two individual convex/concave lenses 1028, 1030. The doublet lens is designed to correct certain aberrations and enhance overall optical performance of the lens assembly. The two lenses 1028, 1030 making up the doublet lens are spaced closely to one another such that the convex curvature of the second convex lens 1028 and the concave curvature of the concave lens 1030 correspond with one another. The convex-concave combination helps control the behavior of EMR passing through the lens assembly.

The doublet serves to correct aberrations, such as spherical aberration, chromatic aberration, and coma. The combination of the two lenses 1028, 1030 with different optical properties helps to counteract the aforementioned aberrations and thus results in improved image quality. Chromatic aberration causes color fringing and blurring of images. By using the double within the positive lens group 810, different colors of light are brought to a common focus to reduce or eliminate chromatic aberration appearing in resultant data frames 205, 207, 209, 211.

The configuration of the doublet lens further serves to reduce the size and weight of the optical visualization system 106. By combining the functions of two individual lenses into a single double lens, the overall size and complexity of the optical visualization system 106 is minimized. The design and optical properties of the doublet lens may vary depending on the specific application and desired performance characteristics. Different combinations of lens elements with varying curvatures, materials, and refractive indices can be used to achieve specific optical goals.

The lens assembly 1000 may be optimized to output the following conditions, wherein $F_p$ is the positive lens group effective focal lens, $F_n$ is the negative lens effective focal length, $P_{nl}$ is the negative lens Petzval curvature, $P_s$ is the whole optical system Petzval curvature, and $F_{cmp}$ is the field angle compression ratio (i.e., the ratio of the field in object space to the field angle in image space).

$$0.9 < \frac{F_p}{F_n} < 1.5$$

$$|P_n| < 0.15$$

$$|P_s| < 0.02$$

$$F_{cmp} < 4.5$$

Figure 11:
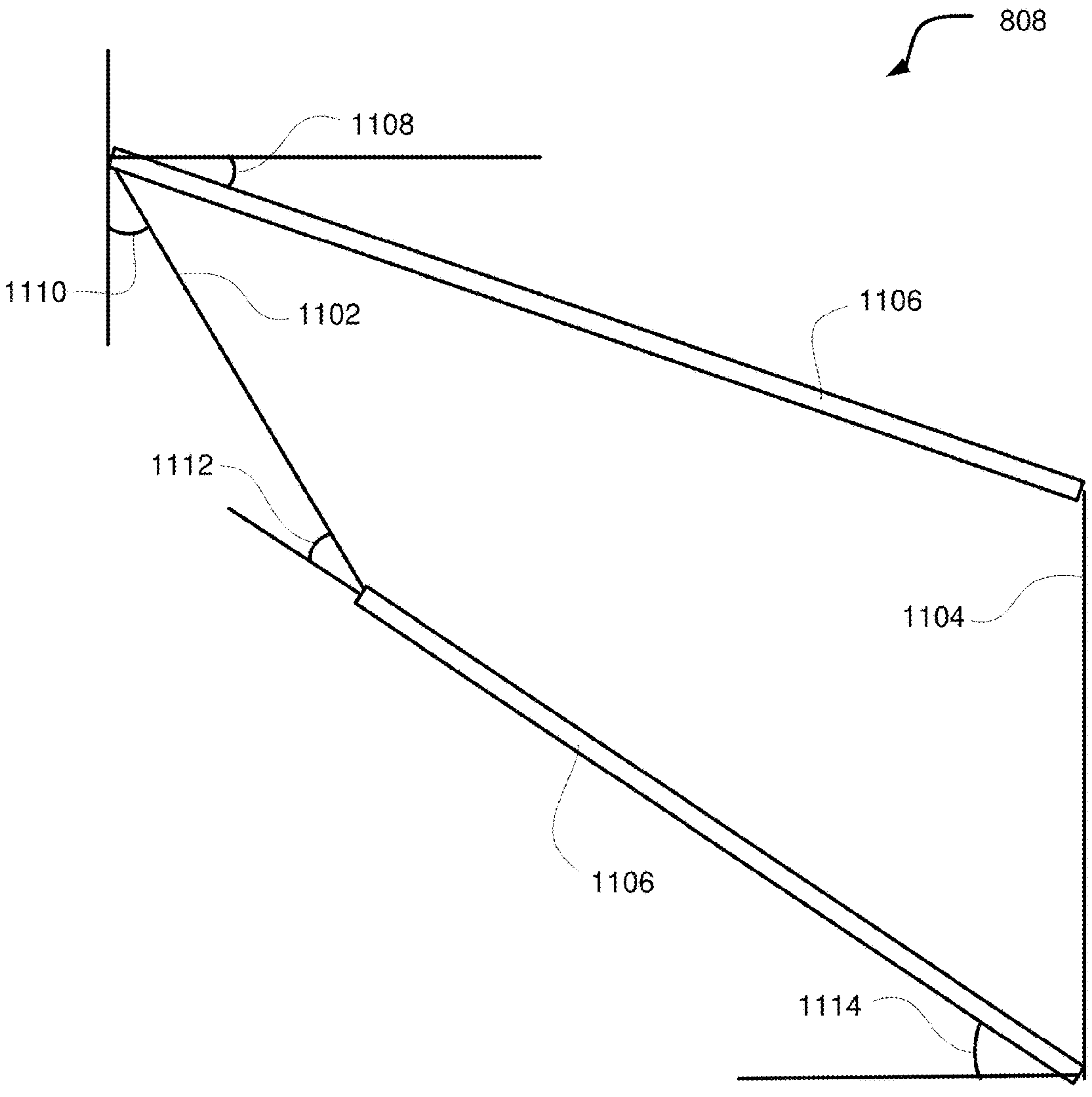
FIG. 11 is a schematic illustration of a 30° direction-of-view prism.

FIG. 11 is a schematic illustration of a cross-sectional side view of the direction-of-view (DOV) prism 808. The prism 808 includes a first face 1102 and a second face 1104 disposed opposite to the first face 1102. The sides 1106 of the prism 808 comprise a reflective coating to aid in bouncing a beam of EMR within the prism 808.

The first exterior angle 1108 may be from about 17° to about 21° and may specifically be 19°. The second exterior angle 1110 may be from about 28° to about 32° and may specifically be 30°. The third exterior angle 1112 may be from about 24° to about 28° and may specifically be 26°. The fourth exterior angle 1114 may be from about 32° to about 36° and may specifically be 34°.

Figure 12:
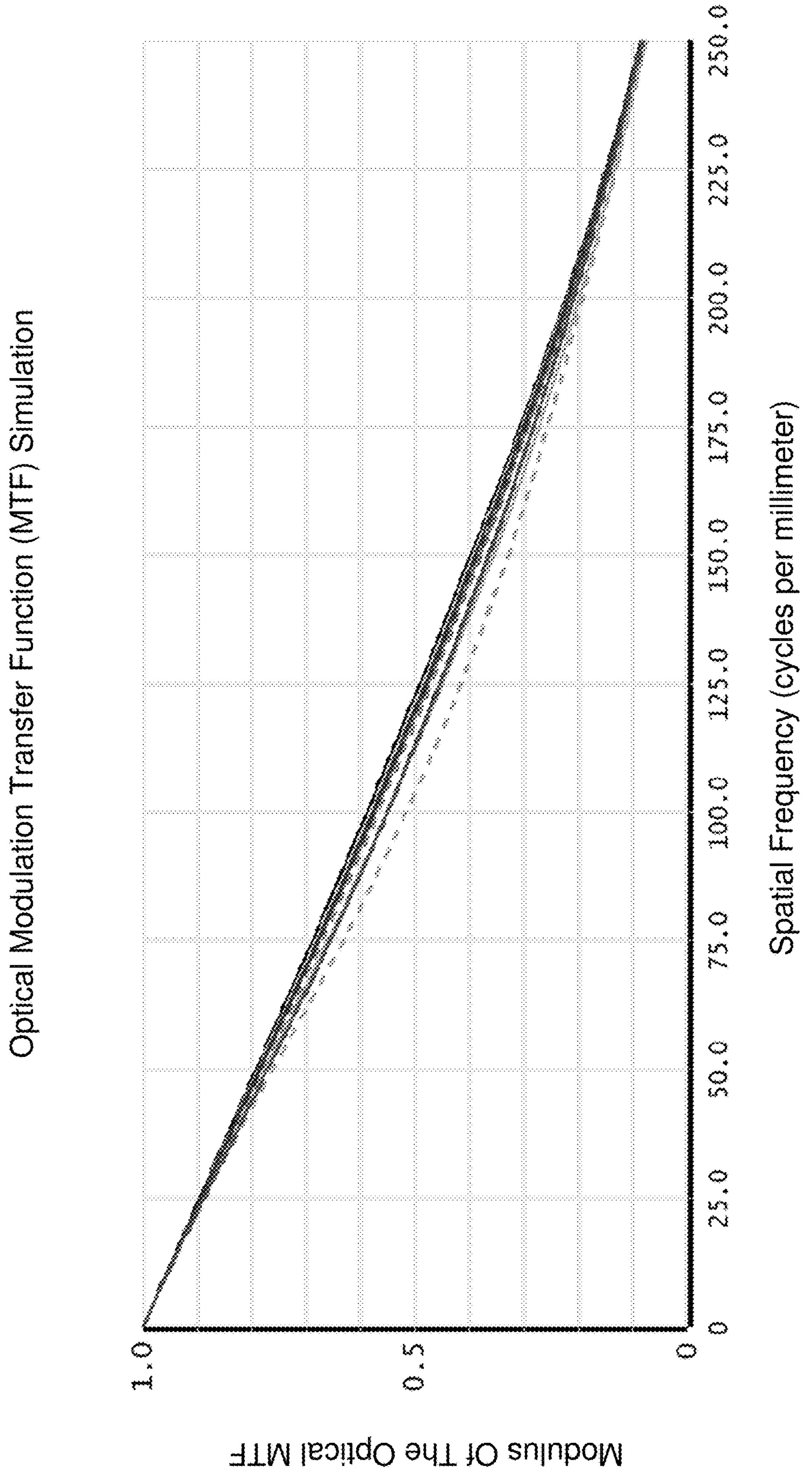
FIG. 12 is a graphical representation of the optical modulation transfer function (MTF) simulation for optical lens assemblies as described herein.

FIG. 12 is a graphical representation of the optical modulation transfer function (MTF) simulation for the optical lens assemblies 800, 900, 1000 described herein. Optical MTF is a quantitative measure of the imaging performance of an optical system and characterizes the system's ability to faithfully transfer spatial details from the object to the image formed. MTF describes the contrast transfer of the system at different spatial frequencies and is often represented graphically as a plot of the MTF values against spatial frequency (as shown in FIG. 12). Spatial frequency refers to the number of cycles per unit distance in the object being imaged.

The MTF curve provides insights into several key aspects of optical performance, including resolution, contrast, frequency response, and aberrations. The MTF curve indicates the system's ability to resolve fine details or spatial frequencies. Higher MTF values at specific spatial frequencies correspond to better resolution and the ability to capture fine details in the image. MTF characterizes the system's ability to maintain contrast as a function of spatial frequency. Higher MTF values at a given frequency indicate better contrast reproduction and higher image fidelity. The MTF curve provides information about the frequency response of the system by showing how different spatial frequencies are transmitted or attenuated by the optical system. MTF can reveal the impact of various optical aberrations, such as spherical aberration, coma, astigmatism, and chromatic aberration. Aberrations tend to degrade MTF performance, resulting in lower contrast and reduced resolution at specific spatial frequencies.

The MTF simulation was performed through laboratory measurements. These measurements include capturing test patterns of known spatial frequencies and analyzing the resulting images to determine the contrast and resolution characteristics.

Figure 13:
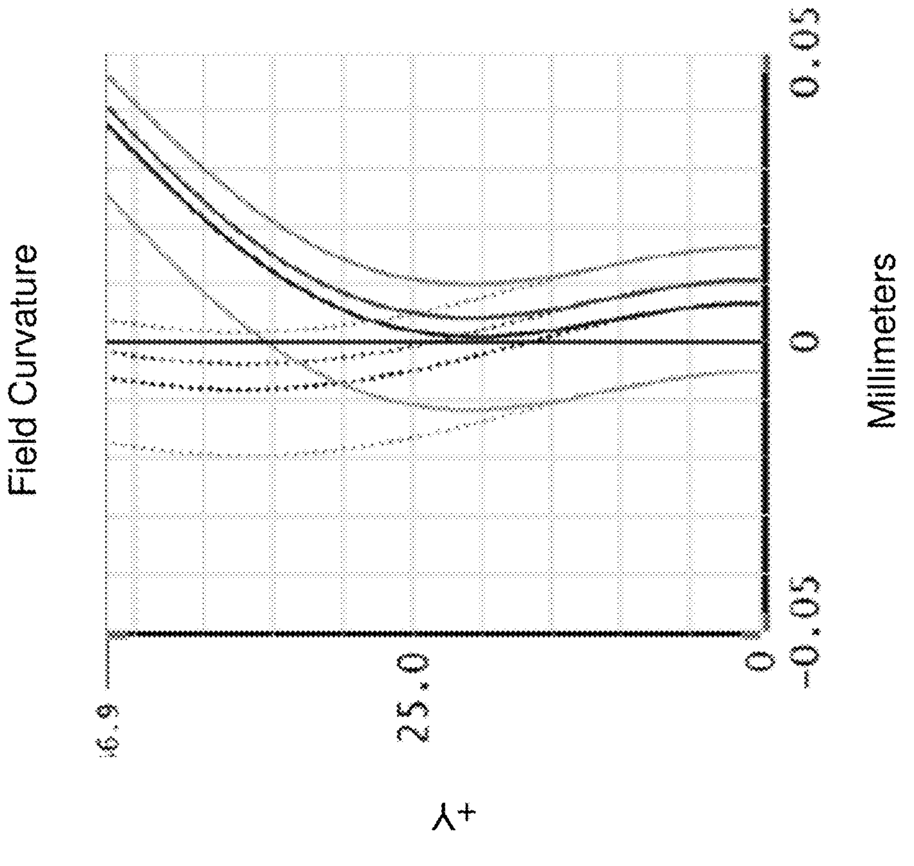
FIG. 13 is a graphical representation of the lens system distortion simulation for the lens assemblies as described herein.

FIG. 13 is a graphical representation of the lens system distortion simulation. FIG. 13 specifically represents the field curvature performance and demonstrates less than 40-micron focal changes over entire 3-milimeter image sensor surface. The focal change refers to the difference between a best fit focal plane and the focal position at the actual curved focal surface. In FIG. 13, the focal change range is from −20 microns to +45 microns. Taking the median of the range, the focal change is ±38 microns. In this study, the lens has an aperture of 6, which has a focal depth of ±40 micron. When considering the pixel size of 1.4 microns with a Bayer pattern color filter array, the effective depth of focus is ±50 microns. This indicates that the lens field curvature meets the needs for this application.

Figure 14:
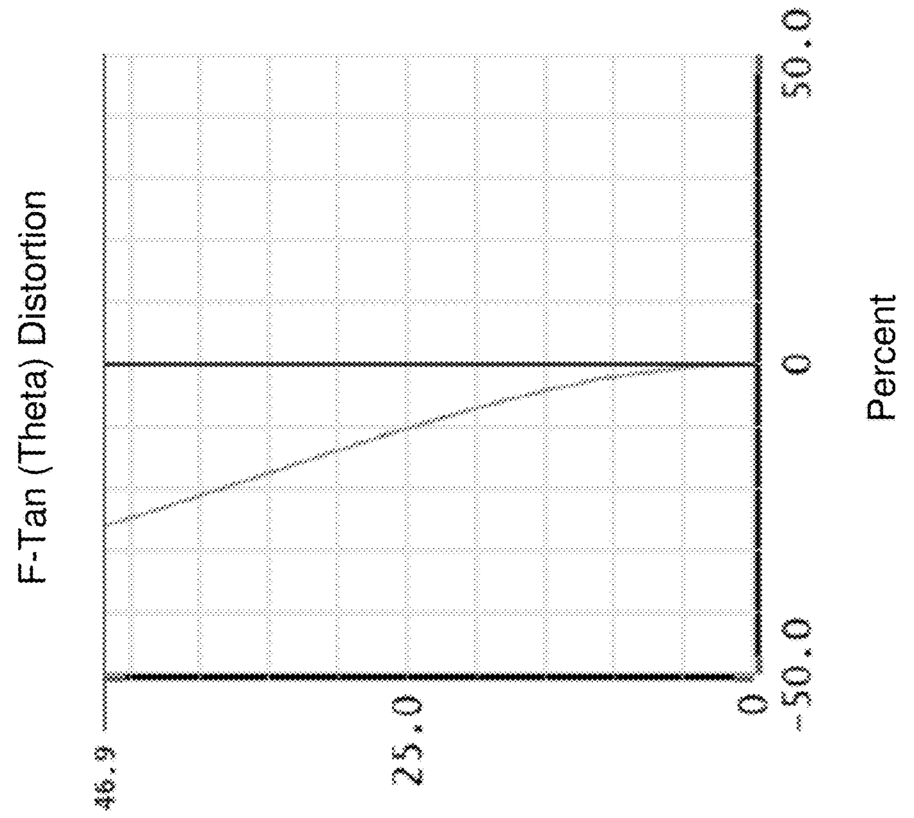
FIG. 14 is a graphical representation of the lens system distortion for the lens assemblies as described herein.

FIG. 14 is a graphical representation of the system distortion. When the lens projects an image on to the image sensor, there will be some distortion. With the lens design described herein, the distortion may be equal to 25% of a 45 mm diameter of field of view. Associated image processing software can correct for this distortion up to 30%. Thus, the lens assembly design described herein may be implemented to optimize robustness without sacrificing image quality.

Figure 15A:
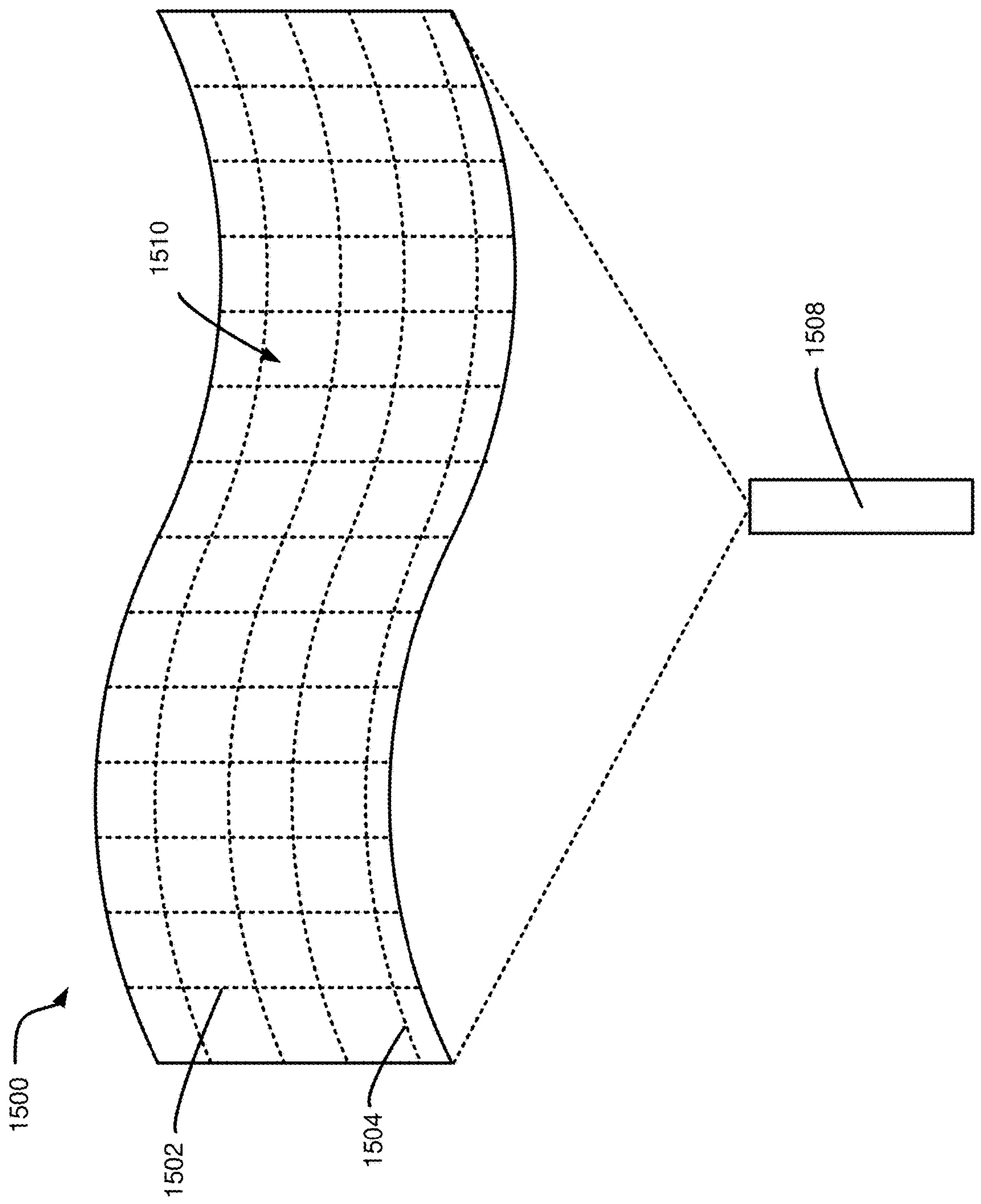
FIG. 15A is a schematic illustration of an example mapping pattern comprising a grid array.
Figure 15B:
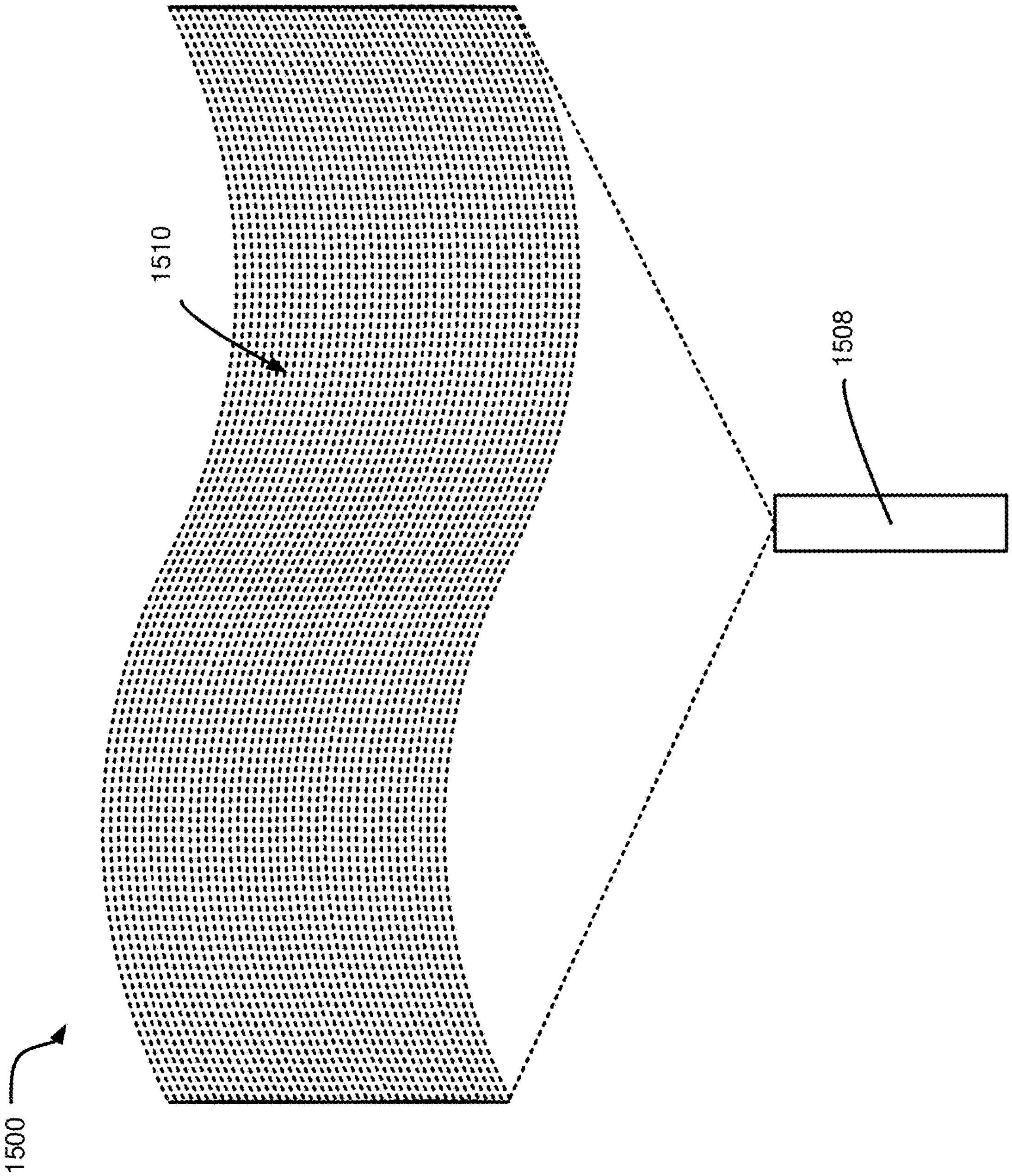
FIG. 15B is a schematic illustration of an example mapping pattern comprising a dot array.

FIGS. 15A and 15B illustrate schematic diagrams of a system 1500 for emitting EMR in a mapping pattern 210. The emitter 102 may pulse the mapping pattern 210 using a low mode laser light that is diffracted to generate the applicable mapping pattern 210. The mapping pattern 210 reflects off tissue in a way that depends on the wavelength of the EMR and the specific anatomical features of the tissue.

The example mapping pattern 210 illustrated in FIG. 15A is a grid array comprising vertical hashing 1502 and horizontal hashing 1504. The example mapping pattern 210 illustrated in FIG. 15B is a dot array. The mapping pattern 210 may include any suitable array for mapping a surface, including, for example, a raster grid of discrete points, an occupancy grid map, a dot array, vertical hashing, horizontal hashing, and so forth. The mapping pattern 210 is emitted by an illumination source 1508, which may originate with an EMR source within the emitter 102 and terminate with an endoscope 110 or tool 108.

As discussed in connection with FIGS. 1A-1C, the distal end of an endoscope 110 may include one or more waveguides 130 that emit EMR that originated at the emitter 102.

The mapping pattern 210 may be emitted from these waveguides 130 and projected on to a surface of a tissue. Additionally, one or more tools 108 within a scene may include a waveguide 131 that terminates at a distal end of the tool 108 and/or a side of the tool 108 as shown in FIG. 1A. This waveguide 131 may also emit the mapping pattern 210 on to a surface of a tissue within a scene. In some cases, the tool 108 and the endoscope 110 emit the mapping pattern 210 in concert, and the resultant data frames captured by the image sensor 124 comprise data for tracking the location of the tool 108 within the scene relative to the endoscope 110 or other tools 108.

The emitter 102 may pulse the mapping pattern 210 at any suitable wavelength of EMR, including, for example, ultraviolet light, visible, light, and/or infrared or near infrared light. The surface and/or objects within the environment may be mapped and tracked at very high resolution and with very high accuracy and precision.

The mapping pattern 210 is selected for the desired anatomical measurement scheme, such as three-dimensional topographical mapping, measuring distances and dimensions within a scene, tracking a relative position of a tool 108 within a scene, and so forth. The image sensor 124 detects reflected EMR and outputs a mapping data frame 211 in response to the emitter 102 pulsing the mapping pattern 210. The resultant mapping data frame 211 is provided to a topographical processing 350 algorithm that is trained to calculate one or more of a three-dimensional topographical map of a scene, a distance between two or more objects within the scene, a dimension of an object within the scene, a relative distance between a tool and another object within the scene, and so forth.

The emitter 102 may pulse the mapping pattern 210 at a sufficient speed such that the mapping pattern 210 is not visible to a user. In various implementations, it may be distracting to a user to see the mapping pattern 210 during an endoscopic visualization procedure. In some cases, a rendering of the mapping pattern 210 may be overlaid on a color video stream to provide further context to a user visualizing the scene. The user may further request to view real-time measurements of objects within the scene and real-time proximity alerts when a tool approaches a critical structure such as a blood vessel, nerve fiber, cancer tissue, and so forth. The accuracy of the measurements may be accurate to less than one millimeter.

Figure 16:
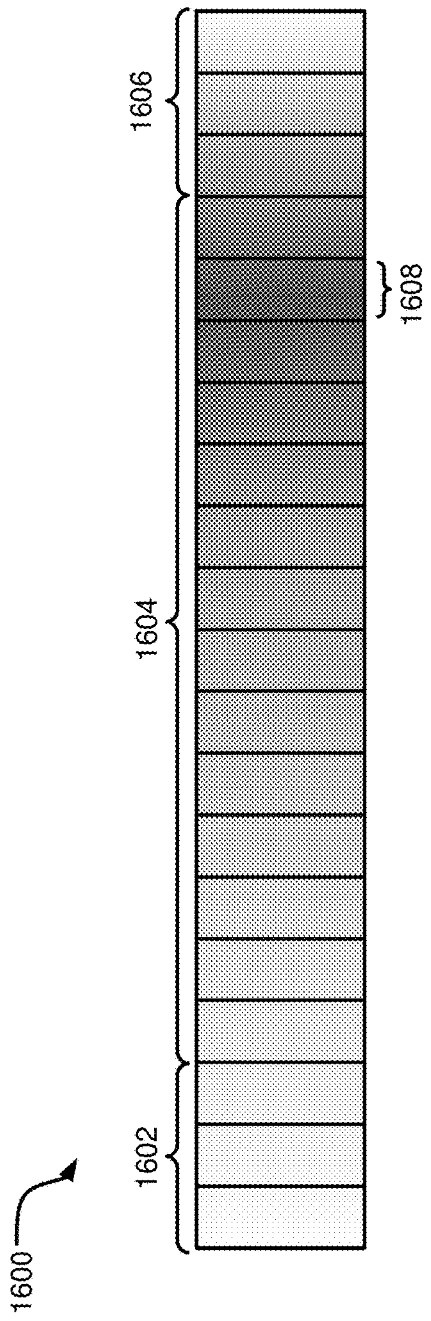
FIG. 16 illustrates a portion of the electromagnetic spectrum divided into a plurality of different wavebands which may be pulsed by sources of electromagnetic radiation of an emitter.

FIG. 16 illustrates a portion of the electromagnetic spectrum 1600 divided into twenty different wavebands. The number of wavebands is illustrative only. In at least one embodiment, the spectrum 1600 may be divided into hundreds of wavebands. The spectrum 1600 may extend from the infrared spectrum 1602, through the visible spectrum 1604, and into the ultraviolet spectrum 1606. Each waveband may be defined by an upper wavelength and a lower wavelength.

Multispectral imaging incudes imaging information from across the electromagnetic spectrum 1600. A multispectral pulse of EMR may include a plurality of sub-pulses spanning one or more portions of the electromagnetic spectrum 1600 or the entirety of the electromagnetic spectrum 1600. A multispectral pulse of EMR may include a single partition of wavelengths of EMR. A resulting multispectral data frame includes information sensed by the pixel array subsequent to a multispectral pulse of EMR. Therefore, a multispectral data frame may include data for any suitable partition of the electromagnetic spectrum 1600 and may include multiple data frames for multiple partitions of the electromagnetic spectrum 1600.

The emitter 102 may include any number of multispectral EMR sources as needed depending on the implementation. In one embodiment, each multispectral EMR source covers a spectrum covering 40 nanometers. For example, one multispectral EMR source may emit EMR within a waveband from 500 nm to 540 nm while another multispectral EMR source may emit EMR within a waveband from 540 nm to 580 nm. In another embodiment, multispectral EMR sources may cover other sizes of wavebands, depending on the types of EMR sources available or the imaging needs. Each multispectral EMR source may cover a different slice of the electromagnetic spectrum 1600 ranging from far infrared, mid infrared, near infrared, visible light, near ultraviolet and/or extreme ultraviolet. In some cases, a plurality of multispectral EMR sources of the same type or wavelength may be included to provide sufficient output power for imaging. The number of multispectral EMR sources needed for a specific waveband may depend on the sensitivity of a pixel array 125 to the waveband and/or the power output capability of EMR sources in that waveband.

The waveband widths and coverage provided by the EMR sources may be selected to provide any desired combination of spectrums. For example, contiguous coverage of a spectrum 1600 using very small waveband widths (e.g., 10 nm or less) may allow for highly selective multispectral and/or fluorescence imaging. The waveband widths allow for selectively emitting the excitation wavelength(s) for one or more particular fluorescent reagents. Additionally, the waveband widths may allow for selectively emitting certain partitions of multispectral EMR for identifying specific structures, chemical processes, tissues, biological processes, and so forth. Because the wavelengths come from EMR sources which can be selectively activated, extreme flexibility for fluorescing one or more specific fluorescent reagents during an examination can be achieved. Additionally, extreme flexibility for identifying one or more objects or processes by way of multispectral imaging can be achieved. Thus, much more fluorescence and/or multispectral information may be achieved in less time and within a single examination which would have required multiple examinations, delays because of the administration of dyes or stains, or the like.

Figure 17:
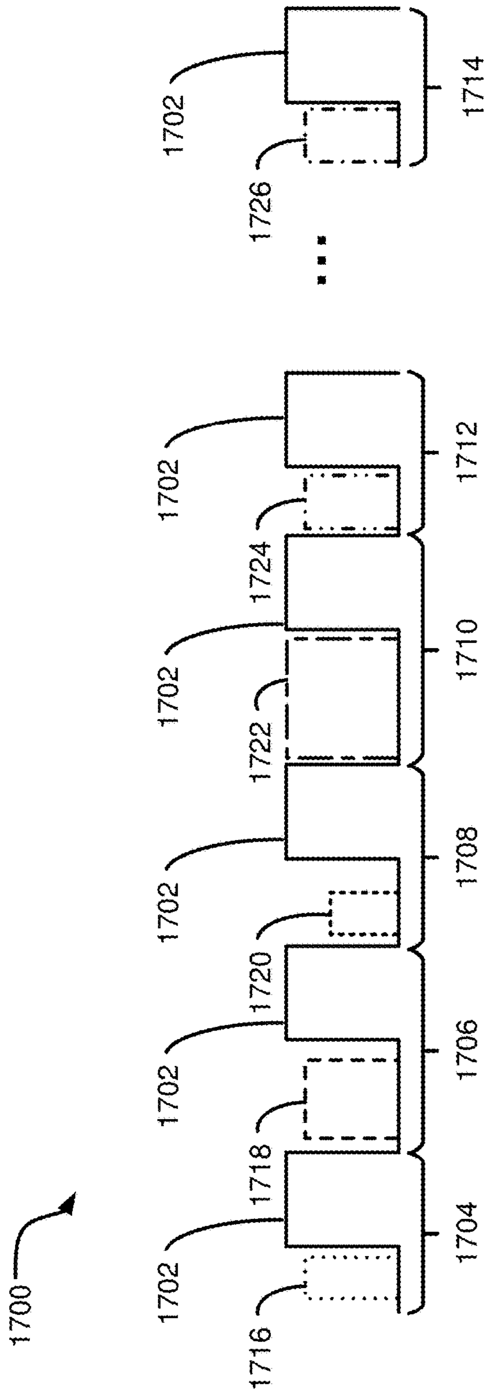
FIG. 17 is a schematic diagram illustrating a timing sequence for emission and readout for generating data frames in response to pulses of electromagnetic radiation.

FIG. 17 is a schematic diagram illustrating a timing diagram 1700 for emission and readout for generating an image. The solid line represents readout (peaks 1702) and blanking periods (valleys) for capturing a series of data frames 1704-1714. The series of data frames 1704-1714 may include a repeating series of data frames which may be used for generating mapping, multispectral, and/or fluorescence data that may be overlaid on an RGB video stream. The series of data frames include a first data frame 1704, a second data frame 1706, a third data frame 1708, a fourth data frame 1710, a fifth data frame 1712, and an Nth data frame 1726.

In one embodiment, each data frame is generated based on at least one pulse of EMR. The pulse of EMR is reflected and detected by the pixel array 125 and then read out in a subsequent readout (1702). Thus, each blanking period and readout results in a data frame for a specific waveband of EMR. For example, the first data frame 1704 may be generated based on a waveband of a first one or more pulses 1716, a second data frame 1706 may be generated based on a waveband of a second one or more pulses 1718, a third data frame 1708 may be generated based on a waveband of a third one or more pulses 1720, a fourth data frame 1710 may be generated based on a waveband of a fourth one or more pulses 1722, a fifth data frame 1712 may be generated based on a waveband of a fifth one or more pulses 1724, and an Nth data frame 1726 may be generated based on a waveband of an Nth one or more pulses 1726.

The pulses 1716-1726 may include energy from a single EMR source or from a combination of two or more EMR sources. For example, the waveband included in a single readout period or within the plurality of data frames 1704-1714 may be selected for a desired examination or detection of a specific tissue or condition. According to one embodiment, one or more pulses may include visible spectrum light for generating an RGB or black and white image while one or more additional pulses are emitted to sense a spectral response to a multispectral wavelength of EMR.

The pulses 1716-1726 are emitted according to a variable pulse cycle determined by the controller 104. For example, pulse 1716 may include a white light, pulse 1718 may include a multispectral waveband, pulse 1720 may include a white light, pulse 1722 may include a fluorescence waveband, pulse 1724 may include white light, and so forth.

The plurality of frames 1704-1714 are shown having varying lengths in readout periods and pulses having different lengths or intensities. The blanking period, pulse length or intensity, or the like may be selected based on the sensitivity of a monochromatic sensor to the specific wavelength, the power output capability of the EMR source(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region. The data output by the dual image sensors is triangulated against the locations of the dual image sensors to calculate relative dimensional information of the scene.

In an example implementation, a patient is imaged with an endoscopic imaging system to identify quantitative diagnostic information about the patient's tissue pathology. In the example, the patient is suspected or known to suffer from a disease that can be tracked with multispectral imaging to observe the progression of the disease in the patient's tissue. The endoscopic imaging system pulses white light to generate an RGB video stream of the interior of the patient's body. Additionally, the endoscopic imaging system pulses one or more multispectral wavebands of light that permit the system to "see through" some tissues and generate imaging of the tissue affected by the disease. The endoscopic imaging system senses the reflected multispectral EMR to generate multispectral imaging data of the diseased tissue, and thereby identifies the location of the diseased tissue within the patient's body. The endoscopic imaging system may further emit a mapping pulsing scheme for generating a three-dimensional topographical map of the scene and calculating dimensions of objects within the scene. The location of the diseased tissue (as identified by the multispectral imaging data) may be combined with the topographical map and dimensions information that is calculated with the mapping data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 18:
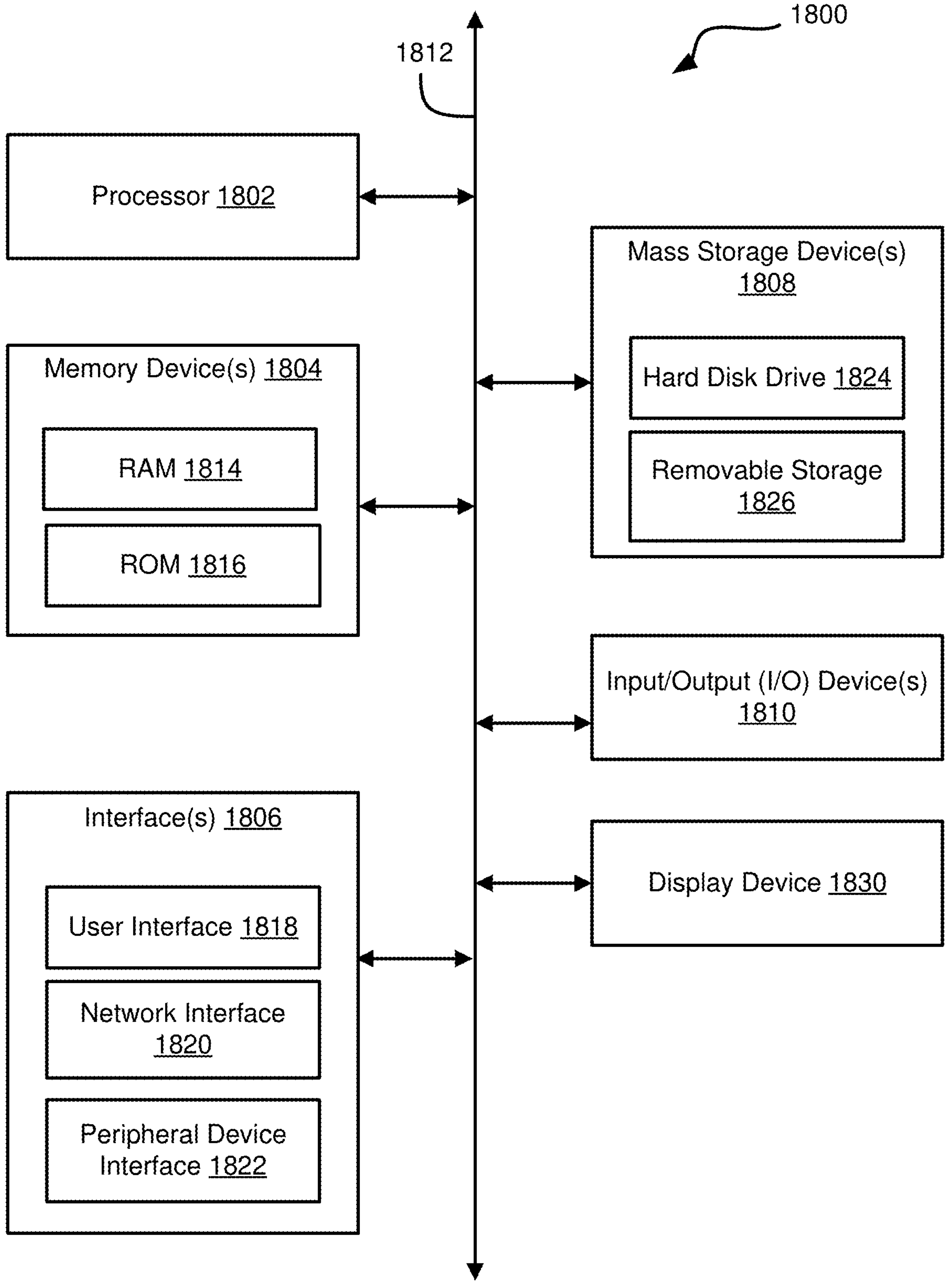
FIG. 18 is a schematic block diagram of an example computing device.

FIG. 18 illustrates a schematic block diagram of an example computing device 1800. The computing device 1800 may be used to perform various procedures, such as those discussed herein. The computing device 1800 can perform various monitoring functions as discussed herein, and can execute one or more application programs, such as the application programs or functionality described herein. The computing device 1800 can be any of a wide variety of computing devices, such as a desktop computer, in-dash computer, vehicle control system, a notebook computer, a server computer, a handheld computer, tablet computer and the like.

The computing device 1800 includes one or more processor(s) 1804, one or more memory device(s) 1804, one or more interface(s) 1806, one or more mass storage device(s) 1808, one or more Input/output (I/O) device(s) 1810, and a display device 1830 all of which are coupled to a bus 1812. Processor(s) 1804 include one or more processors or controllers that execute instructions stored in memory device(s) 1804 and/or mass storage device(s) 1808. Processor(s) 1804 may also include several types of computer-readable media, such as cache memory.

Memory device(s) 1804 include various computer-readable media, such as volatile memory (e.g., random access memory (RAM) 1814) and/or nonvolatile memory (e.g., read-only memory (ROM) 1816). Memory device(s) 1804 may also include rewritable ROM, such as Flash memory.

Mass storage device(s) 1808 include various computer readable media, such as magnetic tapes, magnetic disks, optical disks, solid-state memory (e.g., Flash memory), and so forth. As shown in FIG. 18, a particular mass storage device 1808 is a hard disk drive 1824. Various drives may also be included in mass storage device(s) 1808 to enable reading from and/or writing to the various computer readable media. Mass storage device(s) 1808 include removable media 1826 and/or non-removable media.

I/O device(s) 1810 include various devices that allow data and/or other information to be input to or retrieved from computing device 1800. Example I/O device(s) 1810 include cursor control devices, keyboards, keypads, microphones, monitors or other display devices, speakers, printers, network interface cards, modems, and the like.

Display device 1830 includes any type of device capable of displaying information to one or more users of computing device 1800. Examples of display device 1830 include a monitor, display terminal, video projection device, and the like.

Interface(s) 1806 include various interfaces that allow computing device 1800 to interact with other systems, devices, or computing environments. Example interface(s) 1806 may include any number of different network interfaces 1820, such as interfaces to local area networks (LANs), wide area networks (WANs), wireless networks, and the Internet. Other interface(s) include user interface 1818 and peripheral device interface 1822. The interface(s) 1806 may also include one or more user interface elements 1818. The interface(s) 1806 may also include one or more peripheral interfaces such as interfaces for printers, pointing devices (mice, track pad, or any suitable user interface now known to those of ordinary skill in the field, or later discovered), keyboards, and the like.

Bus 1812 allows processor(s) 1804, memory device(s) 1804, interface(s) 1806, mass storage device(s) 1808, and I/O device(s) 1810 to communicate with one another, as well as other devices or components coupled to bus 1812. Bus 1812 represents one or more of several types of bus structures, such as a system bus, PCI bus, IEEE bus, USB bus, and so forth.

For purposes of illustration, programs and other executable program components are shown herein as discrete blocks, such as block 302 for example, although it is understood that such programs and components may reside at various times in different storage components of computing device 1800 and are executed by processor(s) 1802. Alternatively, the systems and procedures described herein, including programs or other executable program components, can be implemented in hardware, or a combination of hardware, software, and/or firmware. For example, one or more application specific integrated circuits (ASICs) can be programmed to carry out one or more of the systems and procedures described herein.

EXAMPLES

The following examples pertain to preferred features of further embodiments:

Example 1 is a system. The system includes an endoscope tube and an optical assembly disposed within an interior cavity defined by the endoscope tube. The optical assembly includes a negative lens comprising a negative focal length, a positive lens group comprising at least one convex lens, and a beam folding prism that directs a beam of electromagnetic radiation on to a pixel array of an image sensor.

Example 2 is a system as in Example 1, further comprising two or more image sensors, wherein each of the two or more image sensors is disposed within the interior cavity defined by the endoscope tube.

Example 3 is a system as in any of Examples 1-2, wherein the optical assembly further comprises a transparent window disposed at a distal end of the endoscope tube; and wherein the transparent window receives the beam of electromagnetic radiation prior to any other component of the optical assembly.

Example 4 is a system as in any of Examples 1-3, wherein the optical assembly further comprises an aperture stop plate.

Example 5 is a system as in any of Examples 1-4, wherein the aperture stop plate is disposed adjacent to the negative lens such that the beam of electromagnetic radiation first passes through the negative lens and converges on a surface of the aperture stop plate.

Example 6 is a system as in any of Examples 1-5, wherein the optical assembly further comprises a reject filter that prevents a selected waveband of electromagnetic radiation from irradiating the pixel array of the image sensor.

Example 7 is a system as in any of Examples 1-6, wherein the reject filter prevents near infrared electromagnetic radiation from irradiating the pixel array.

Example 8 is a system as in any of Examples 1-7, wherein the reject filter prevents a fluorescence excitation emission of electromagnetic radiation from irradiating the pixel array; and wherein the fluorescence excitation emission comprises electromagnetic radiation within a waveband from about 770 nm to about 815 nm.

Example 9 is a system as in any of Examples 1-8, wherein the reject filter permits visible electromagnetic radiation to pass through the reject filter and irradiate the pixel array.

Example 10 is a system as in any of Examples 1-9, wherein the positive lens group comprises a doublet lens, and wherein the double lets comprises one convex lens and one concave lens.

Example 11 is a system as in any of Examples 1-10, wherein the positive lens group comprises the at least one convex lens in addition to the doublet lens.

Example 12 is a system as in any of Examples 1-11, further comprising: a first image sensor; a second image sensor; and a processor in communication with the first image sensor and the second image sensor; wherein each of the first image sensor and the second image sensor simultaneously output a data frame comprising pixel integration data; and wherein the processor calculates dimensional information for a scene by triangulating the pixel integration data simultaneously output by the first image sensor and the second image sensor.

Example 13 is a system as in any of Examples 1-12, wherein the optical assembly comprises a first channel dedicated to the first image sensor and a second channel dedicated to the second image sensor.

Example 14 is a system as in any of Examples 1-13, wherein the optical assembly comprises: the first channel dedicated to the first image sensor, wherein the first channel comprises: a first negative lens comprising the negative focal length; a first positive lens group comprising at least one convex lens; and a first beam folding prism that directs the beam of electromagnetic radiation on to the first image sensor; and the second channel dedicated to the second image sensor, wherein the second channel comprises: a second negative lens comprising the negative focal length; a second positive lens group comprising at least one convex lens; and a second beam folding prism that directs the beam of electromagnetic radiation on to the second image sensor.

Example 15 is a system as in any of Examples 1-14, wherein the optical assembly further comprises: the first channel dedicated to the first image sensor, wherein the first channel further comprises: a first reject filter that prevents a selected waveband of electromagnetic radiation from irradiating the first image sensor; and a first aperture stop plate; the second channel dedicated to the second image sensor, wherein the second further channel comprises: a second reject filter that prevents a selected waveband of electromagnetic radiation from irradiating the second image sensor; and a second aperture stop plate.

Example 16 is a system as in any of Examples 1-15, wherein a first aperture for the first aperture stop plate is independently adjustable relative to a second aperture for the second aperture stop plate.

Example 17 is a system as in any of Examples 1-16, wherein the first reject filter is configured to reject a different waveband of electromagnetic radiation relative to the second reject filter.

Example 18 is a system as in any of Examples 1-17, further comprising a direction-of-view prism configured to define a direction of view for visualization data output by the image sensor, wherein the direction of view is defined relative to a longitudinal axis of the endoscope tube.

Example 19 is a system as in any of Examples 1-18, wherein the direction-of-view prism defines a 0° direction-of-view adjustment relative to the longitudinal axis of the endoscope tube.

Example 20 is a system as in any of Examples 1-19, wherein the direction-of-view prism defines a 30° direction-of-view adjustment relative to the longitudinal axis of the endoscope tube.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim.

Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system for endoscopic visualization, the system comprising:

an endoscope tube; and an optical assembly disposed within an interior cavity defined by the endoscope tube, the optical assembly comprising:

a negative lens comprising a negative focal length;

an aperture stop plate;

a direction-of-view prism;

a positive lens group comprising at least one convex lens; and a beam folding prism that directs a beam of electromagnetic radiation onto a pixel array of an image sensor;

wherein, along an optical axis of the optical assembly, the negative lens, the aperture stop plate, the direction-of-view prism, and the positive lens group are arranged sequentially.

2. The system of claim 1, further comprising two or more image sensors, wherein each of the two or more image sensors is disposed within the interior cavity defined by the endoscope tube.

3. The system of claim 1, wherein the optical assembly further comprises a transparent window disposed at a distal end of the endoscope tube; and wherein the transparent window receives the beam of electromagnetic radiation prior to any other component of the optical assembly.

4. The system of claim 1, wherein the aperture stop plate is configured to align components of the optical assembly.

5. The system of claim 1, wherein the optical assembly further comprises a reject filter that prevents a selected waveband of electromagnetic radiation from irradiating the pixel array of the image sensor.

6. The system of claim 5, wherein the reject filter prevents a fluorescence excitation emission of electromagnetic radiation from irradiating the pixel array; and wherein the fluorescence excitation emission comprises electromagnetic radiation within a waveband from about 770 nm to about 815 nm.

7. The system of claim 5, wherein the reject filter permits visible electromagnetic radiation to pass through the reject filter and irradiate the pixel array.

8. The system of claim 1, wherein the positive lens group comprises a doublet lens, and wherein the doublet lens comprises one convex lens and one concave lens.

9. The system of claim 8, wherein the positive lens group comprises the at least one convex lens in addition to the doublet lens.

10. The system of claim 1, further comprising:

a first image sensor;

a second image sensor; and a processor in communication with the first image sensor and the second image sensor;

wherein each of the first image sensor and the second image sensor simultaneously output a data frame comprising pixel integration data; and wherein the processor calculates dimensional information for a scene by triangulating the pixel integration data simultaneously output by the first image sensor and the second image sensor.

11. The system of claim 10, wherein the optical assembly comprises a first channel dedicated to the first image sensor and a second channel dedicated to the second image sensor.

12. The system of claim 11, wherein the optical assembly comprises:

the first channel dedicated to the first image sensor, wherein the first channel comprises:

a first negative lens comprising the negative focal length;

a first positive lens group comprising at least one convex lens; and a first beam folding prism that directs the beam of electromagnetic radiation on to the first image sensor; and the second channel dedicated to the second image sensor, wherein the second channel comprises:

a second negative lens comprising the negative focal length;

a second positive lens group comprising at least one convex lens; and a second beam folding prism that directs the beam of electromagnetic radiation on to the second image sensor.

13. The system of claim 12, wherein the optical assembly further comprises:

the first channel dedicated to the first image sensor, wherein the first channel further comprises:

a first reject filter that prevents a first selected waveband of electromagnetic radiation from irradiating the first image sensor; and a first-plate;

the second channel dedicated to the second image sensor, wherein the second further channel comprises:

a second reject filter that prevents a second selected waveband of electromagnetic radiation from irradiating the second image sensor; and a second plate.

14. The system of claim 13, wherein the first plate is a first aperture stop plate and the second plate is a second aperture stop plate, and wherein the first aperture stop plate comprises a first aperture that is independently adjustable relative to a second aperture for the second aperture stop plate.

15. The system of claim 1, wherein the direction-of-view prism is configured to define a direction of view and a direction of view adjustment for visualization data output by the image sensor, and wherein the direction of view adjustment comprises an angle from about 0 degrees to about 90 degrees.

16. The system of claim 1, wherein beam folding prism is disposed after the positive lens group along the optical axis.

17. A system for endoscopic visualization, the system comprising:

an endoscope tube; and an optical assembly disposed within an interior cavity defined by the endoscope tube, the optical assembly comprising:

a negative lens comprising a negative focal length;

a plate;

an angle-selecting prism comprising a coating that reflects a beam of electromagnetic radiation;

a positive lens group comprising at least one convex lens; and a beam folding prism that directs a beam of electromagnetic radiation onto a pixel array of an image sensor.

18. The system of claim 17, further comprising:

a first image sensor;

a second image sensor; and a processor in communication with the first image sensor and the second image sensor;

wherein the optical assembly is a first optical assembly and a second optical assembly;

wherein the first optical assembly is dedicated to the first image sensor and the second optical assembly is dedicated to the second image sensor;

wherein each of the first image sensor and the second image sensor simultaneously output a data frame comprising pixel integration data; and wherein the processor calculates dimensional information for a scene by triangulating the pixel integration data simultaneously output by the first image sensor and the second image sensor.

19. A system comprising:

an endoscope tube;

a processor; and an optical assembly disposed within an interior cavity defined by the endoscope tube, the optical assembly comprising:

a negative lens comprising a negative focal length;

a positive lens group comprising at least one convex lens; and a beam folding prism that directs a beam of electromagnetic radiation onto a pixel array of an image sensor;

wherein the processor corrects optical effects introduced by the beam folding prism.

20. The system of claim 19, further comprising:

a plate, wherein the plate is one or both of a match plate and an aperture stop plate, and a direction-of-view prism.

* * * * *